(12) United States Patent
Wang et al.

(10) Patent No.: US 11,408,859 B2
(45) Date of Patent: Aug. 9, 2022

(54) ULTRASONIC PROBE COUPLING ASSEMBLY AND ULTRASONIC PROBE ASSEMBLY

(71) Applicant: SHENZHEN LEPUYUAN MEDICAL TECHNOLOGY CO., LTD., Guangdong (CN)

(72) Inventors: Caifeng Wang, Shenzhen (CN); Zhigang Luo, Shenzhen (CN); Junying Ma, Shenzhen (CN)

(73) Assignee: SHENZHEN LEPUYUAN MEDICAL TECHNOLOGY CO., LTD., Shenzhen (CN)

( * ) Notice: Subject to any disclaimer, the term of this patent is extended or adjusted under 35 U.S.C. 154(b) by 163 days.

(21) Appl. No.: 16/767,138

(22) PCT Filed: May 15, 2019

(86) PCT No.: PCT/CN2019/087046
§ 371 (c)(1),
(2) Date: May 27, 2020

(87) PCT Pub. No.: WO2020/052260
PCT Pub. Date: Mar. 19, 2020

(65) Prior Publication Data
US 2020/0386717 A1    Dec. 10, 2020

(30) Foreign Application Priority Data

Sep. 14, 2018 (CN) .......................... 201811075233.2
Sep. 14, 2018 (CN) .......................... 201821518450.X
(Continued)

(51) Int. Cl.
*G01N 29/22* (2006.01)
*A61B 8/00* (2006.01)

(52) U.S. Cl.
CPC ......... *G01N 29/223* (2013.01); *G01N 29/225* (2013.01); *A61B 8/4444* (2013.01)

(58) Field of Classification Search
CPC .. G01N 29/223; G01N 29/225; A61B 8/4444; A61B 8/4272; A61B 8/4281
See application file for complete search history.

(56) References Cited

U.S. PATENT DOCUMENTS 5,739,463 A * 4/1998 Diaz .................... H05K 5/0039
                                                           174/378
2017/0303894 A1   10/2017 Scully
(Continued)

FOREIGN PATENT DOCUMENTS

CN      202875380 U     4/2013
CN      204121059 U     1/2015
(Continued)

*Primary Examiner* — Suman K Nath
(74) *Attorney, Agent, or Firm* — Merchant & Gould P.C.

(57) ABSTRACT

An ultrasonic probe coupling assembly (1) and an ultrasonic probe mechanism are disclosed. The ultrasonic probe coupling assembly (1) includes a probe sleeve (11) and a solid-state coupling member (12). The probe sleeve (11) is sleeved on an ultrasonic probe (2). The solid-state coupling member (12) is fixed in the probe sleeve (11). One side of the solid-state coupling member (12) is located in the probe sleeve (11) for fitting to the ultrasonic probe (2), and the other side is protruded from the probe sleeve (11) to be in contact with the skin. The ultrasonic probe mechanism includes the ultrasonic probe coupling assembly (1) and the ultrasonic probe (2).

18 Claims, 9 Drawing Sheets

(30) Foreign Application Priority Data

Dec. 25, 2018 (CN) .......................... 201811594295.4
Dec. 25, 2018 (CN) .......................... 201822193936.7
Dec. 25, 2018 (CN) .......................... 201822208898.8

(56) References Cited

U.S. PATENT DOCUMENTS

| | | | | |
|---|---|---|---|---|
| 2017/0360415 A1* | 12/2017 | Rothberg | ................ | A61B 8/12 |
| 2018/0000451 A1 | 1/2018 | Choi | | |
| 2019/0353854 A1* | 11/2019 | Radelet | ................ | G02B 6/4471 |

FOREIGN PATENT DOCUMENTS

| | | |
|---|---|---|
| CN | 204121060 U | 1/2015 |
| CN | 104606022 A | 5/2015 |
| CN | 206355070 U | 7/2017 |
| CN | 107411775 A | 12/2017 |
| CN | 107616813 A | 1/2018 |
| CN | 207118999 U | 3/2018 |
| CN | 207400752 U | 5/2018 |
| CN | 108135569 A | 6/2018 |
| CN | 108324322 A | 7/2018 |
| CN | 109091166 A | 12/2018 |
| CN | 109480905 A | 3/2019 |
| CN | 209220326 U | 8/2019 |

* cited by examiner

ULTRASONIC PROBE COUPLING ASSEMBLY AND ULTRASONIC PROBE ASSEMBLY

PRIORITY

This application is a U.S. national application of the international application number PCT/CN2019/087046 filed on May 15, 2019 and claiming priority of respectively Chinese applications CN201811075233.2 filed on Sep. 14, 2018; CN201822208898.8 filed on Dec. 25, 2018; CN201811594295.4 filed on Dec. 25, 2018; CN201822193936.7 filed on Dec. 25, 2018 and CN201821518450.X filed on Sep. 14, 2018 the contents of all of which are incorporated herein by reference.

TECHNICAL FIELD

The present disclosure relates to the field of ultrasound detection equipment, and particularly to an ultrasonic probe coupling assembly and an ultrasonic probe mechanism.

BACKGROUND ART

Ultrasonic examination is a guarantee for information acquisition for doctors, and is also crucial in diagnosis of diseases. At present, in cardiac ultrasonic examination and superficial examination, since the range of the field of view of a phased array near field is very small and artifacts are easily generated in the near field, the blood flow around cardiac apex can hardly be seen clearly, accurate judgment can hardly be made on the condition of blood flow of some main arteries, and the blood flow under the skin cannot be clearly seen by a linear array probe, which bring great trouble to the doctor's diagnosis work.

At present, during the process of ultrasonic examination, the examination site needs to be coated with a gel-like coupling agent first, then an ultrasonic probe slides thereon for examination, and when the examination is finished, the examination site needs to be cleaned with a large amount of paper towels. The gel-like coupling agent applied during the examination leads to a viscous and greasy feeling, resulting in poor user experience.

In the prior art, a solid-state coupling patch is laid on the surface of the examination site to fill the gap between the probe and the body surface, but when in use, the solid-state coupling patch needs to be moved as the examination site changes, which is relatively troublesome; and moving the solid-state coupling patch by hand will contaminate the solid-state coupling patch. There is also a solution of securing the solid-state coupling patch to the probe via a connector. However, due to the difference in type of different probes and the assembly difference between the solid-state coupling patch and the probe, the solid-state coupling patch cannot form a good fit with the probe, making it impossible to achieve the desired solid-state coupling effect.

SUMMARY

In view of at least one deficiency of the prior art, the present disclosure provides an ultrasonic probe coupling assembly and an ultrasonic probe assembly, so as to solve the problems of discomfort caused by the use of a gel-like coupling agent, inconvenience in the use of a solid-state coupling patch and poor fit between the solid-state coupling patch and a probe in the prior art.

To this end, the present disclosure provides the following technical solution:

an ultrasonic probe coupling assembly, comprising a probe clamping sleeve and a solid-state coupling member, wherein the probe clamping sleeve is configured to be sleeved on an ultrasonic probe; and the solid-state coupling member is fixed in the probe clamping sleeve, with one side being located in the probe clamping sleeve to be attached to the ultrasonic probe, and the other side protruding from the probe clamping sleeve for contact with the skin.

As an alternative solution of the above-described ultrasonic probe coupling assembly, the solid-state coupling member is fixed in the probe clamping sleeve by injection molding.

As an alternative solution of the above-described ultrasonic probe coupling assembly, the solid-state coupling member comprises a fixing portion and a protruding portion that are integrally molded, the fixing portion is molded to be connected in the probe clamping sleeve and is configured to be attached to the ultrasonic probe, and the protruding portion protrudes from the probe clamping sleeve for contact with the skin.

As an alternative solution of the above-described ultrasonic probe coupling assembly, the solid-state coupling member comprises a plastic portion and a solid-state coupling portion, the plastic portion is embedded in the solid-state coupling portion, so that the solid-state coupling member is integrally formed, the plastic portion is formed as an annular protrusion of the solid-state coupling member, and the solid-state coupling member is fixed in the probe clamping sleeve by the plastic portion.

As an alternative solution of the above-described ultrasonic probe coupling assembly, the ultrasonic probe coupling assembly further comprises a pressing member, the pressing member is fixed at an end portion of the probe clamping sleeve for pressing the solid-state coupling member, and the solid-state coupling member protrudes from the pressing member.

As an alternative solution of the above-described ultrasonic probe coupling assembly, the ultrasonic probe coupling assembly further comprises an elastic gasket, the elastic gasket is provided on the probe clamping sleeve, and when the ultrasonic probe is inserted into the probe clamping sleeve, the elastic gasket is sandwiched between the probe clamping sleeve and the ultrasonic probe.

As an alternative solution of the above-described ultrasonic probe coupling assembly, the radius of curvature of the side of the solid-state coupling member in contact with the ultrasonic probe is not smaller than the radius of curvature of the ultrasonic probe, and the radius of curvature of the side of the solid-state coupling member in contact with the skin is not greater than the radius of curvature of the ultrasonic probe.

As an alternative solution of the above-described ultrasonic probe coupling assembly, the ultrasonic probe coupling assembly is applicable to a phased array probe, a linear array probe and a convex array probe, and the probe clamping sleeve has a structure matching the phased array probe, the linear array probe or the convex array probe.

The ultrasonic probe coupling assembly and the ultrasonic probe mechanism of the present disclosure have at least the following advantages:

The ultrasonic probe coupling assembly is connected to the ultrasonic probe by means of plugging-in, and has relatively good assemblability. By pushing the ultrasonic probe, the end portion of the ultrasonic probe is attached to the solid-state coupling member located at the inner side of the probe clamping sleeve, so that seamless transition is realized between the ultrasonic probe and the skin, air between the ultrasonic probe and the skin is eliminated, and stable and effective transmission of the ultrasonic waves is ensured.

The ultrasonic probe assembly comprises the ultrasonic probe coupling assembly, there is no need to use a gel coupling agent, and the solid-state coupling member used is capable of forming a good fit with the ultrasonic probe.

In the present disclosure, the solid-state coupling member is fixed, by the probe clamping sleeve, on the ultrasonic probe for use, thereby solving the problems of discomfort caused by the use of a gel-like coupling agent, inconvenience in the use of a solid-state coupling patch and poor fit between the solid-state coupling patch and a probe in the prior art. However, due to the variety of the types of the ultrasonic probes, when manufactured by different manufacturers, the ultrasonic probes of the same type still differ in size, and a different ultrasonic probe still needs to be configured with a probe clamping sleeve having a size corresponding to the ultrasonic probe.

In view of this, an object of the present disclosure is to overcome the above-mentioned deficiencies, and provide an adaptive ultrasonic probe coupling assembly and an ultrasonic probe mechanism capable of improving the use experience and optimizing the ultrasonic wave transmission effect, wherein the ultrasonic probe coupling assembly can be adapted to ultrasonic probes of a variety of sizes and types.

The present disclosure provides the following technical solution:

an ultrasonic probe coupling assembly, comprising a probe clamping sleeve, a solid-state coupling member and an elastic gasket, wherein the elastic gasket is disposed on the probe clamping sleeve, and the elastic gasket is disposed between the probe clamping sleeve and the ultrasonic probe when the probe clamping sleeve is sleeved on the ultrasonic probe; and the solid-state coupling member is fixed in the probe clamping sleeve, with one side being located in the probe clamping sleeve to be attached to the ultrasonic probe, and the other side protruding from the probe clamping sleeve for contact with the skin.

As an alternative solution of the above-described ultrasonic probe coupling assembly, the elastic gasket is a rubber gasket or a foam gasket.

As an alternative solution of the above-described ultrasonic probe coupling assembly, the elastic gasket is connected to the probe clamping sleeve by plugging-in.

As an alternative solution of the above-described ultrasonic probe coupling assembly, the probe clamping sleeve is provided with an inserting groove, and the elastic gasket is correspondingly provided with an inserting block.

As an alternative solution of the above-described ultrasonic probe coupling assembly, the inserting groove is provided with a position-limiting groove, and the inserting block is inserted into the position-limiting groove so as to limit the elastic gasket from being separated from the probe clamping sleeve.

As an alternative solution of the above-described ultrasonic probe coupling assembly, the inserting groove is provided with a position-limiting groove, the inserting block is correspondingly provided with a position-limiting protrusion protruding from the inserting block, and when the inserting block is inserted into the inserting groove, the position-limiting protrusion is embedded in the position-limiting groove.

As an alternative solution of the above-described ultrasonic probe coupling assembly, the elastic gasket is detachable from the probe clamping sleeve.

As an alternative solution of the above-described ultrasonic probe coupling assembly, the elastic gasket located at the inner side of the probe clamping sleeve has an outwardly flared guiding slope at the end close to an opening surface of the probe clamping sleeve, and the elastic gasket extending towards the inner side of the probe clamping sleeve has a clamping surface that matches the ultrasonic probe.

As an alternative solution of the above-described ultrasonic probe coupling assembly, the elastic gasket is an elastic sleeve that covers an opening of the probe clamping sleeve; or a plurality of elastic gaskets are provided in a circumferential direction of the opening of the probe clamping sleeve.

The adaptive ultrasonic probe coupling assembly and the ultrasonic probe mechanism of the present disclosure have at least the following advantages:

By providing an elastic gasket, the elastic gasket has a certain clamping size margin, and can form an adaptive clamping for the ultrasonic probes that do not differ greatly in size, and for the ultrasonic probes that differ greatly in size, elastic gaskets different in thickness can be used to adapting, so that the ultrasonic probe coupling assembly of the present disclosure can be adapted to ultrasonic probes of a variety of sizes and types, thereby forming ultrasonic probe mechanisms having the same ultrasonic probe coupling assembly and different ultrasonic probe sizes.

In view of the deficiencies in the prior art, the present disclosure provides an ultrasonic probe coupling assembly and an ultrasonic probe assembly, so as to solve the problems of discomfort caused by the use of a gel-like coupling agent, inconvenience in the use of a solid-state coupling patch and poor fit between the solid-state coupling patch and a probe in the prior art.

To this end, the present disclosure provides the following technical solution:

an ultrasonic probe coupling assembly, comprising a probe clamping sleeve and a solid-state coupling member, wherein the probe clamping sleeve is configured to be sleeved on an ultrasonic probe, and the solid-state coupling member comprises a plastic portion and a solid-state coupling portion;

the plastic portion is embedded in the solid-state coupling portion, so that the solid-state coupling member is integrally formed, the plastic portion is formed as an annular protrusion of the solid-state coupling member, and the plastic portion is deformable together with the solid-state coupling portion;

one side of the solid-state coupling portion is located in the probe clamping sleeve to be attached to the ultrasonic probe, and the other side of the solid-state coupling portion protrudes from the probe clamping sleeve for contact with the skin; and the inner side of the probe clamping sleeve is provided with an adjusting locking groove comprising a plurality of locking positions, and by engaging with different locking positions, the plastic portion is capable of adjusting the position of the solid-state coupling member relative to the probe clamping sleeve and/or the curvature of the solid-state coupling member.

As an alternative solution of the above-described ultrasonic probe coupling assembly, the ultrasonic probe coupling assembly further comprises a pressing member, the pressing member is provided with claws cooperating with the locking positions of the adjusting locking groove; and the pressing member is deformable and covers the plastic portion, and the plastic portion is fixed to the probe clamping sleeve by the pressing member.

As an alternative solution of the above-described ultrasonic probe coupling assembly, the ultrasonic probe is a flat convex array probe, and the cross sections of the probe clamping sleeve, the solid-state coupling member and the pressing member match the cross section of the convex array probe; and a short shaft of the pressing member is provided with a fixing claw, and a long shaft of the pressing member is provided with an adjusting claw, and a fixing locking groove capable of engaging with the fixing claw and an adjusting locking groove capable of engaging with the adjusting claw are provided at corresponding positions of the probe clamping sleeve.

As an alternative solution of the above-described ultrasonic probe coupling assembly, two adjusting claws on the pressing member are inclined, oppositely and inwardly, or a top surface of the adjusting locking groove is inclined outwardly from the solid-state coupling member to the ultrasonic probe.

As an alternative solution of the above-described ultrasonic probe coupling assembly, the solid-state coupling portion comprises a probe engaging portion and a skin engaging portion provided on the two sides of the plastic portion, the probe engaging portion is attached to the ultrasonic probe, and the skin engaging portion is attached to the skin; and each of the two ends of the skin engaging portion is provided with a lobe, and the lobe is not higher than a middle bulge of the skin engaging portion.

As an alternative solution of the above-described ultrasonic probe coupling assembly, the ultrasonic probe is a linear array probe, and the cross sections of the probe clamping sleeve, the solid-state coupling member and the pressing member match the cross section of the linear array probe.

As an alternative solution of the above-described ultrasonic probe coupling assembly, the adjusting locking groove comprises continuous ratchet teeth provided at the inner side of the probe clamping sleeve, the ratchet teeth are inclined in a direction away from the ultrasonic probe.

As an alternative solution of the above-described ultrasonic probe coupling assembly, the ultrasonic probe coupling assembly further comprises an elastic gasket, the elastic gasket is disposed at the inner side of the probe clamping sleeve and detachable from the probe clamping sleeve, and when the ultrasonic probe is inserted into the probe clamping sleeve, the elastic gasket is disposed between the ultrasonic probe and the probe clamping sleeve.

As an alternative solution of the above-described ultrasonic probe coupling assembly, a plurality of T-shaped grooves are circumferentially provided at the inner side of the probe clamping sleeve, and the elastic gasket matches the T-shaped groove.

The present disclosure further provides the following technical solution:

an ultrasonic probe assembly, comprising an ultrasonic probe and the above-described ultrasonic probe coupling assembly.

The ultrasonic probe clamping sleeve assembly and the ultrasonic probe assembly of the present disclosure have at least the following advantages:

While fixing the solid-state coupling member to the ultrasonic probe, the ultrasonic probe clamping sleeve assembly can be adapted to convex array probes having different curvatures, and can also eliminate the assembly difference between the ultrasonic probe (including the convex array probe and the linear array probe) and the ultrasonic probe clamping sleeve, and the processing difference of the ultrasonic probe clamping sleeve assembly, enabling a better fit between the solid-state coupling member and the ultrasonic probe.

The ultrasonic probe assembly comprises the ultrasonic probe clamping sleeve assembly, there is no need to use a gel coupling agent, and the solid-state coupling member used is capable of forming a good fit with the ultrasonic probe.

In order to make the above objects, features and advantages of the present disclosure more apparent and understandable, detailed description is made below in connection with preferred embodiments with reference to the accompanying drawings.

BRIEF DESCRIPTION OF DRAWINGS

In order to more clearly illustrate the technical solutions of the embodiments of the present disclosure, brief description is made below on the drawings required to be used in the embodiments. It should be understood that the following drawings only illustrate some of the embodiments of the present disclosure and shall not be regarded as a limitation to the scope, and for a person of ordinary skills in the art, other related drawings may be obtained from these drawings without inventive effort.

Figure 1:
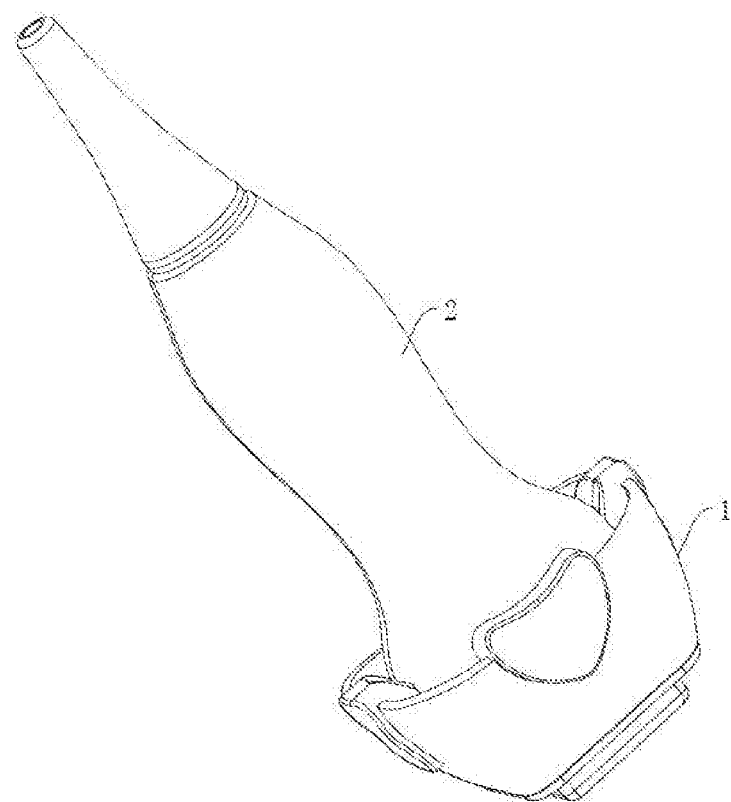
FIG. 1 is an overall structure schematic view of an ultrasonic probe mechanism provided by the present disclosure.

Reference signs: 1—ultrasonic probe coupling assembly; 11—probe clamping sleeve; 111—adjusting locking groove; 112—fixing locking groove; 113—inserting groove; 114—position-limiting groove; 115—connecting frame; 116—connecting rib; 117—L-shaped rib; 12—solid-state coupling member; 120—relief groove; 121—plastic portion; 122—solid-state coupling portion; 1221—probe engaging portion; 1222—skin engaging portion; 12221—lobe; 123—fixing portion; 124—protruding portion; 13—pressing member; 131—adjusting claw; 132—fixing claw; 14—elastic gasket; 141—inserting block; 142—position-limiting protrusion; and 2—ultrasonic probe.

DETAILED DESCRIPTION OF EMBODIMENTS

Hereinafter, various embodiments of the present disclosure will be described more comprehensively with reference to the drawings. The present disclosure may have various embodiments, and adjustments and changes may be made therein. Accordingly, the present disclosure will be described in more detail with reference to the specific embodiments shown in the drawings. It should be understood, however, that there is no intention to limit the various embodiments of the present disclosure to the particular embodiments of the present disclosure, rather, the present disclosure should be understood to cover all adjustments, equivalents and/or alternatives falling within the spirit and scope of the various embodiments of the present disclosure. The same reference signs denote the same elements in the description in conjunction with the drawings.

Preferred embodiments of the ultrasonic probe coupling assembly and the ultrasonic probe assembly are shown in the drawings. However, the ultrasonic probe coupling assembly and the ultrasonic probe assembly may be implemented in many different forms and are not limited to the embodiments described herein. On the contrary, the purpose of providing these embodiments is to make the disclosure of the ultrasonic probe coupling assembly and the ultrasonic probe assembly more thorough and comprehensive.

It should be noted that when an element is referred to as being "fixed to" another element, it can be directly on the another element or there can also be an intermediate element. When one element is regarded as being "connected" to another element, it can be directly connected to the another element or there may also be an intermediate element. However, when an element is referred to as being "directly on" another element, there is no intermediate element. The terms "vertical", "horizontal", "left", "right" and the like expression used herein are only for illustrative purpose.

Hereinafter, the term "include" or "may include" that may be used in various embodiments of the present disclosure indicates the presence of the disclosed function, operation or element, without limiting the addition of one or more functions, operations or elements. In addition, as used in the various embodiments of the present disclosure, the terms "include", "comprise" and cognate words thereof are merely intended to denote specific features, numbers, steps, operations, elements, components or combinations of foregoing items, and should not be construed as first excluding the possibility of the presence of one or more other features, numbers, steps, operations, elements, components or combinations of foregoing items, or the possibility of the addition of one or more features, numbers, steps, operations, elements, components or combinations of foregoing items.

In various embodiments of the present disclosure, the expression "or" or "at least one of A or/and B" includes any combination or all combinations of concurrently listed words. For example, the expression "A or B" or "at least one of A or/and B" may include A, B, or both A and B.

The expressions (such as "first", "second", etc.) used in various embodiments of the present disclosure may modify various components in the various embodiments, without limiting the corresponding components. For example, the above expressions do not limit the order and/or importance of the components. The above expressions merely serve the purpose of distinguishing one component from the other components. For example, the first user device and the second user device indicate different user devices, although both are user devices. For example, the first element may be referred to as the second element, and similarly, the second element may also be referred to as the first element, without departing from the scope of the various embodiments of the present disclosure.

It should be noted that if it is described that one component is "connected" to another component, it is possible that the first component is directly connected to the second component and that a third component may be "connected" between the first component and the second component. On the contrary, when a component is "directly connected" to another component, it can be understood that there is no third component between the first component and the second component.

The terms used in the various embodiments of the present disclosure merely serve the purpose of describing the specific embodiments and are not intended to limit the various embodiments of the present disclosure. As used herein, singular forms are intended to include plural forms as well, unless the context clearly indicates otherwise. Unless otherwise defined, all the terms (including technical and scientific terms) used herein have the same meaning as commonly understood by those of ordinary skills in the technical field of the various embodiments of the present disclosure. The terms (such as those defined in commonly used dictionaries) will be interpreted as having the same meaning as contextual meaning in the related technical field and will not be interpreted as having an idealized or overly formal meaning unless otherwise clearly defined in various embodiments of the present disclosure.

Figure 2:
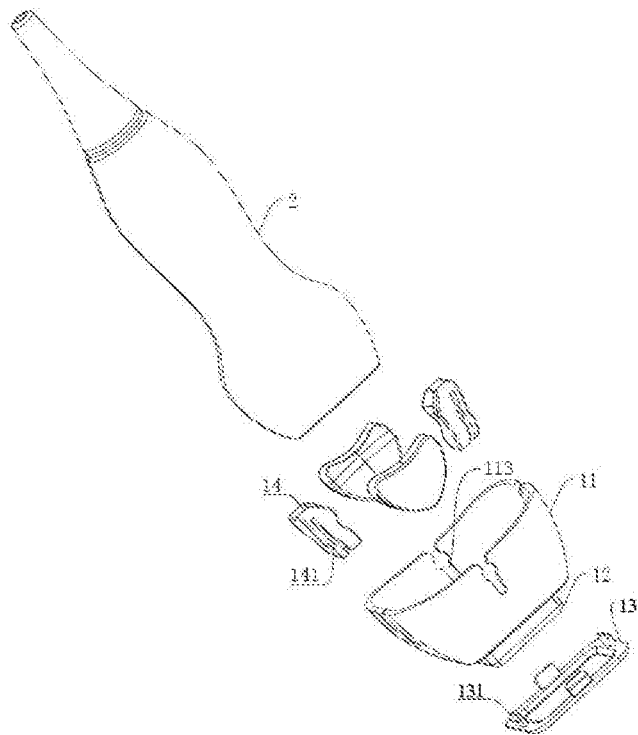
FIG. 2 is an exploded structure schematic view of the ultrasonic probe mechanism provided by the present disclosure.

Referring to FIGS. 1 and 2 together, the present disclosure provides an ultrasonic probe mechanism, comprising an ultrasonic probe coupling assembly 1 and an ultrasonic probe 2. By connecting the ultrasonic probe coupling assembly 1 to the ultrasonic probe 2, the use of an ultrasonic coupling agent can be omitted. The ultrasonic probe coupling assembly 1 comprises a probe clamping sleeve 11 and a solid-state coupling member 12. The solid-state coupling member 12 is fixed to the probe clamping sleeve 11, and the probe clamping sleeve 11 is sleeved on the ultrasonic probe 2, thereby fixing the solid-state coupling member 12 to the ultrasonic probe 2.

One side of the solid-state coupling member 12 is located in the probe clamping sleeve 11 for attachment to the ultrasonic probe 2, and the other side of the solid-state coupling member 12 protrudes from the probe clamping sleeve 11 for contact with the skin. At the time of mounting the ultrasonic probe coupling assembly 1 on the ultrasonic probe 2, the ultrasonic probe 2 is inserted into the probe clamping sleeve 11, and by pushing the ultrasonic probe 2, the end portion of the ultrasonic probe 2 is attached to the solid-state coupling member 12 located at the inner side of the probe clamping sleeve 11, so that seamless transition is realized between the ultrasonic probe 2 and the skin, air between the ultrasonic probe 2 and the skin is eliminated, and stable and effective transmission of the ultrasonic waves is ensured.

Optionally, the solid-state coupling member 12 is fixed in the probe clamping sleeve 11 by injection molding. The solid-state coupling member 12 is a solid-state coupling gel. At the beginning of injection molding, the coupling gel is flowable, and while being set, the coupling gel forms a force to engage with the probe clamping sleeve 11, thereby being fixed in the probe clamping sleeve 11 to form the solid-state coupling member 12.

Figure 3:
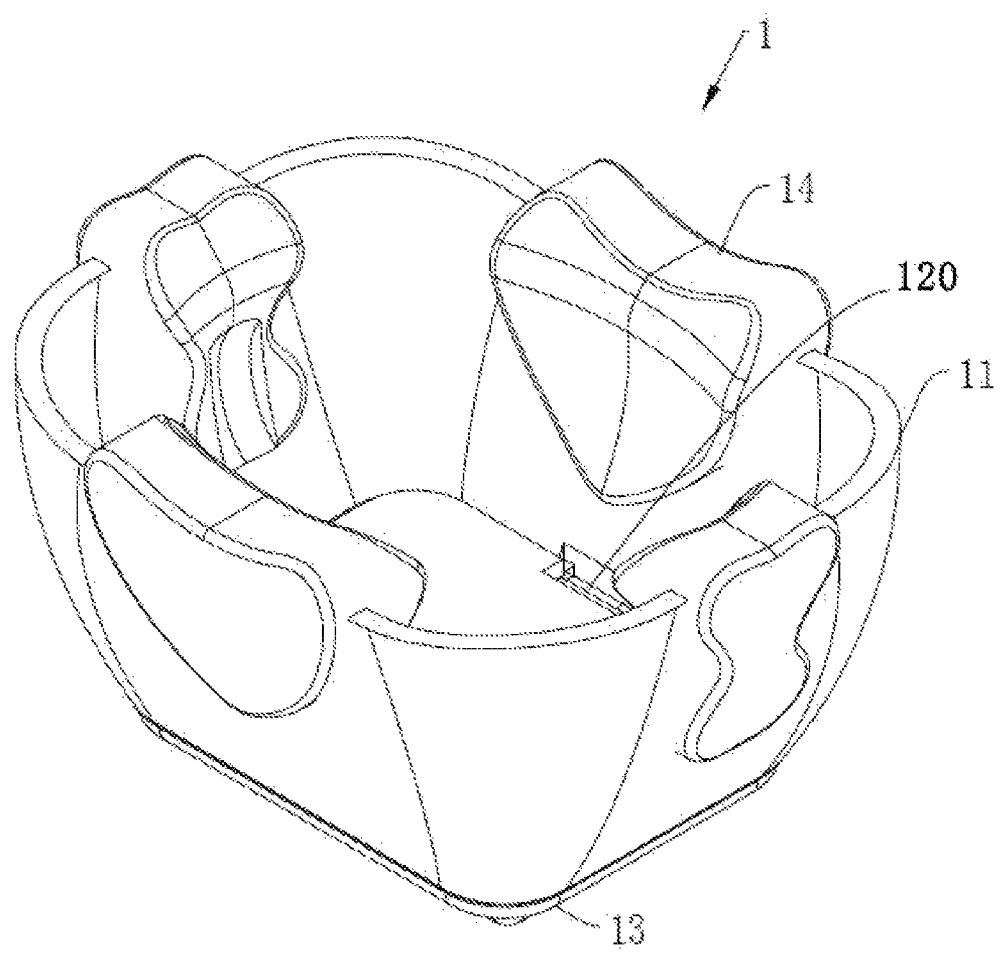
FIG. 3 is an axonometric structure schematic view of an ultrasonic probe coupling assembly provided by the present disclosure.
Figure 4:
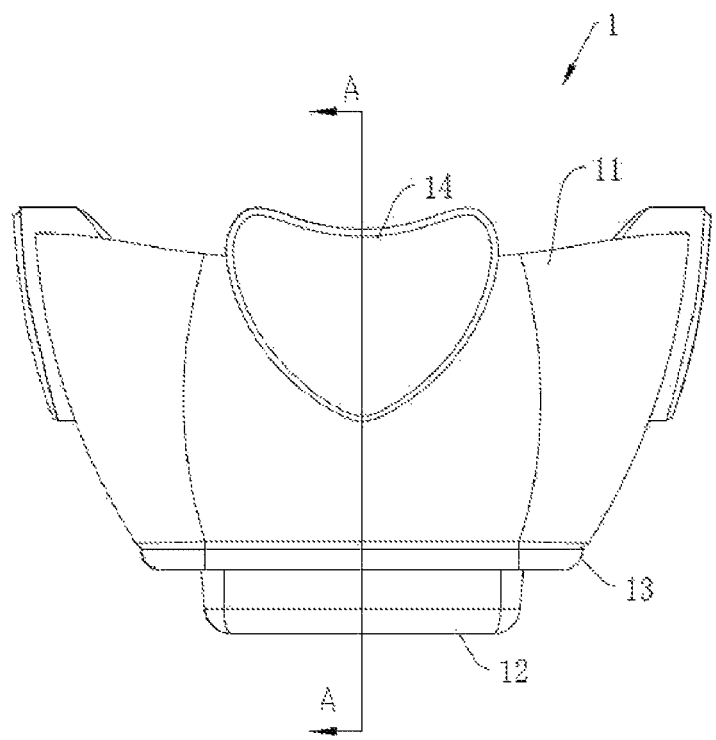
FIG. 4 is a front view of the ultrasonic probe coupling assembly provided by the present disclosure.
Figure 5:
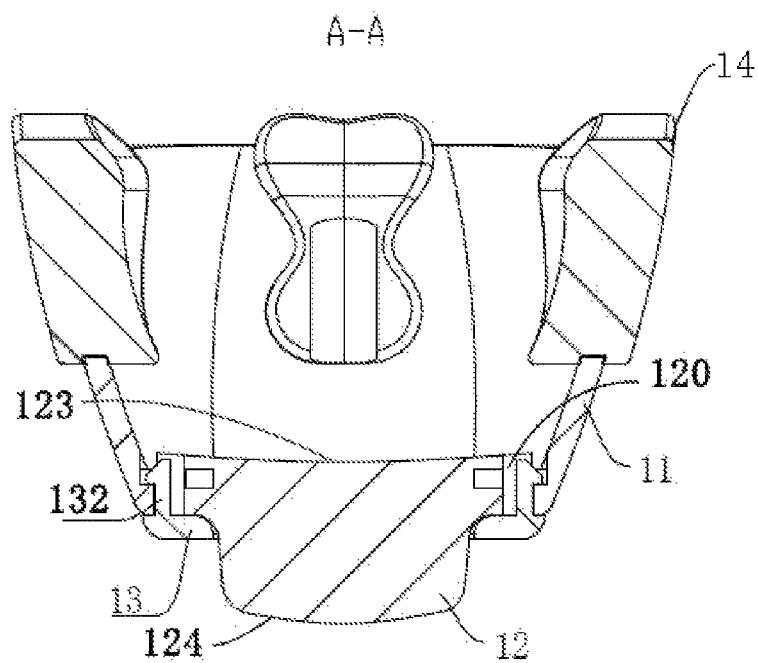
FIG. 5 is an A-A sectional structure schematic view of FIG. 4.

Referring to FIGS. 3-5 together, the solid-state coupling member 12 is injection molded on the probe clamping sleeve 11, omitting the assembly of the solid-state coupling member 12 on the probe clamping sleeve 11, and effectively avoiding contamination to the solid-state coupling member 12 during the assembly of the solid-state coupling member 12. Due to the characteristic of soft nature of the solid-state coupling member 12, it is also possible to effectively overcome the problem of damages to the solid-state coupling member 12 at the time of assembly, and the problem of inaccurate assembly of the solid-state coupling member 12 as the solid-state coupling member 12 is susceptible to deformation at the time of assembly.

Moreover, the solid-state coupling member 12 uses the probe clamping sleeve 11 as a part of the injection mold, enabling the solid-state coupling member 12 to be more appropriately sized with the probe clamping sleeve 11. Further, the solid-state coupling member 12 is directly molded on the probe clamping sleeve 11, enabling the formation of seamless connection between the probe clamping sleeve 11 and the solid-state coupling member 12, thereby enabling the solid-state coupling member 12 to have better ultrasonic transmission effect.

The solid-state coupling member 12 comprises a fixing portion 123 and a protruding portion 124 that are integrally formed. The fixing portion 123 is molded to be connected in the probe clamping sleeve 11 for being attached to the ultrasonic probe 2, and the protruding portion 124 protrudes from the probe clamping sleeve 11 for contacting the skin. The solid-state coupling member 12 is fixed to the probe clamping sleeve 11 by the fixing portion 123, and contacts the skin by the protruding portion 124, so that the ultrasonic waves of the ultrasonic probe 2 sequentially pass through the fixing portion 123 and the protruding portion 124 and then are transmitted to the skin.

In order to enhance the injection-molding connection force between the fixing portion 123 and the probe clamping sleeve 11, a plurality of communicating grooves/recesses may be provided on the probe clamping sleeve 11, so that the solid-state coupling member 12 and the probe clamping sleeve 11 have a greater engagement force. The communicating grooves/recesses on the probe clamping sleeve 11 may also have a barbed structure, so that the solid-state coupling member 12 can form a barbed connection with the probe clamping sleeve 11 during injection molding.

Optionally, a connecting frame 115 is provided/molded at a position of the probe clamping sleeve 11 close to the end surface, the connecting frame 115 is provided at the inner side of the end portion of the probe clamping sleeve 11 and is connected to the inner wall of the probe clamping sleeve 11 by a plurality of connecting ribs 116, and the probe clamping sleeve 11 may be an integrally molded plastic member. The connecting frame 115, the probe clamping sleeve 11 and the connecting ribs 116 form a plurality of through grooves/recesses, some of the through grooves/recesses are used for connecting the pressing member 13 (mentioned hereinafter), and some of the through grooves/recesses enable filling of the coupling gel therein at the time of injection molding the solid-state coupling member 12, thereby enhancing the fixing effect of the solid-state coupling member 12.

Optionally, after being molded by casting, the solid-state coupling member 12 may also wrap the connecting frame 115, exposing only the recesses/through grooves on the connecting frame 115 that need to be connected to the pressing member 13, thereby further ensuring the fixing effect of the solid-state coupling member 12 and the probe clamping sleeve 11.

In addition, the distance from the connecting frame 115 to the end surface of the probe clamping sleeve 11 matches the thickness of the fixing portion 123, so that the fixing portion 123 is embedded in the probe clamping sleeve 11, preventing the fixing portion 123 from protruding from the probe clamping sleeve 11 to interfere with the contact between the protruding portion 124 and the skin.

Optionally, the ultrasonic probe coupling assembly 1 further comprises a pressing member 13, the pressing member 13 is fixed to the end portion of the probe clamping sleeve 11 for pressing the fixing portion 123, the protruding portion 124 protruding from the pressing member 13. The pressing member 13 further fixes the solid-state coupling member 12 to the ultrasonic probe coupling assembly 1 while covering the fixing portion 123, so that the protruding portion 124 protrudes from the pressing member 13.

Figure 6:
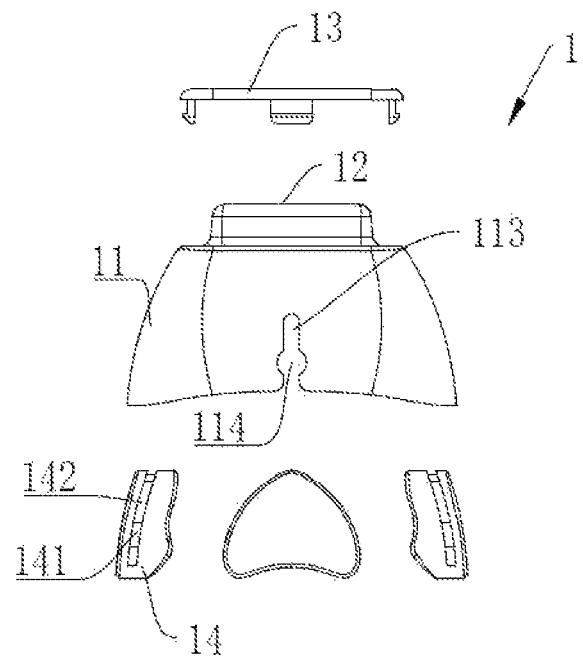
FIG. 6 is a first exploded structure schematic view of the ultrasonic probe coupling assembly provided by the present disclosure.
Figure 7:
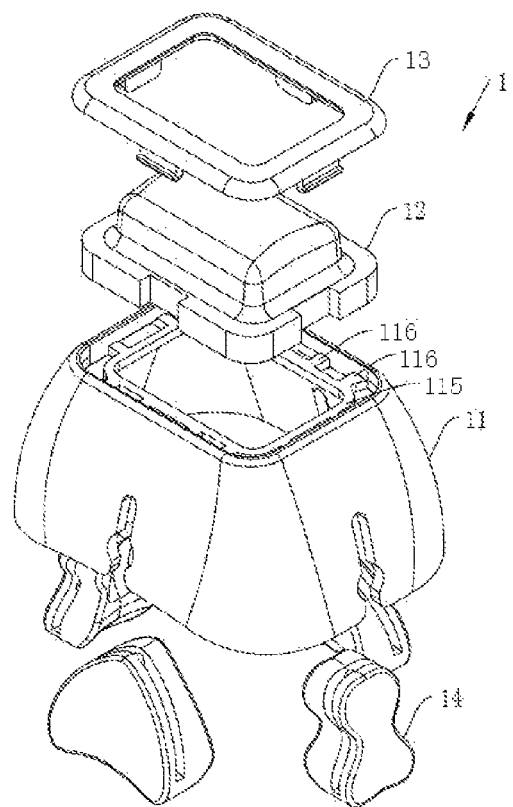
FIG. 7 is a second exploded structure schematic view of the ultrasonic probe coupling assembly provided by the present disclosure.

Referring to FIGS. 6 and 7 together, in order to clearly illustrate the structure of the probe clamping sleeve 11 and the solid-state coupling member 12, the solid-state coupling member 12 is detached from the probe clamping sleeve 11 in the figures.

Optionally, the pressing member 13 is connected to the probe clamping sleeve 11 by clamping, and the pressing member 13 is provided with a plurality of fixing claws 132 and is connected to the probe clamping sleeve 11 by the fixing claws 132, thereby fixing the solid-solid coupling member 12 to the probe clamping sleeve 11. As mentioned above, the probe clamping sleeve 11 is provided with the connecting frame 115, the connecting frame 115, the connecting ribs 116 and the inner wall of the probe clamping sleeve 11 form a plurality of through grooves/recesses, and the fixing claws 132 on the pressing member 13 can be clamped in the through grooves/recesses, thereby achieving fixing to the probe clamping sleeve 11. It should be noted that, at the time of molding the solid-state coupling member 12, a relief groove 120 allowing the fixing claws 132 to pass through and to be inserted into the probe clamping sleeve 11 is directly molded on the fixing portion 123 of the solid-state coupling member 12.

Optionally, when fixed to the probe clamping sleeve 11, the pressing member 13 can compress the fixing portion 123 to a certain extent, and the fixing portion 123 is extruded to produce a certain elastic deformation, while producing an elastic restoring force, so that the pressing member 13 and the solid-state coupling member 12 interact and support each other to form a better fixing effect.

Specifically, the thickness of the fixing portion 123 is larger than the maximum distance between the pressing member 13 and the connecting frame 115 when the pressing member 13 is connected to the probe clamping sleeve 11, thereby effectively preventing displacement of the pressing member 13, and well fixing the solid-state coupling member 12.

The pressing member 13 is made of rigid plastic and may be made of the same material as the probe clamping sleeve 11, e.g., common plastics such as PC (polycarbonate), PVC (polyvinyl chloride), PP (polypropylene) or PE (polyethylene). When engaging with the probe clamping sleeve 11, the rigid pressing member 13 can provide a firmer fixing force for the solid-state coupling member 12.

Optionally, the fixing portion 123 is molded on the connecting frame 115 without wrapping the connecting frame 115, the shape and size of the opening of the probe clamping sleeve 11 match the protruding portion 124, the shape and size of the opening of the probe clamping sleeve 11 is the shape and size of the interior of the connecting frame 115 on the probe clamping sleeve 11, and the portion of the fixing portion 123 facing the interior of the probe clamping sleeve 11 is exposed from the connecting frame 115. That is, the shape and size of the portion of the solid-state coupling member 12 exposed in the probe clamping sleeve 11 are limited by the connecting frame 115, and are the same as the shape and size of the interior of the connecting frame 115.

The size of the end portion of the ultrasonic probe 2 does not exceed the size of the inner frame of the connecting frame 115, i.e., not larger than the size of the protruding portion 124. Thus, the acoustic waves emitted from the ultrasonic probe 2 can all pass through the fixing portion 123 and the protruding portion 124 and are then transmitted to the outside.

Optionally, the ultrasonic probe 2 assembly is applied to a cardiac ultrasonic probe or a linear array probe, the end surface of the cardiac ultrasonic probe or the linear array probe is a plane, the end surface of the probe clamping sleeve 11 is a plane, the solid-state coupling member 12 is formed by two stacked cuboids, the cuboid having a larger size is the fixing portion 123, and a plurality of relief grooves 120 allowing the fixing claws 132 of the pressing member 13 to pass through are provided on the fixing portion 123 in the circumferential direction. The cuboid having a smaller size is the protruding portion 124. The pressing member 13 is a square frame, and a fixing claw 132 is provided on the surface of the frame.

It will be appreciated that the ultrasonic probe 2 assembly may also be applied to other types of ultrasonic probes 2, e.g., phased array probes or convex array probes, the shape of the end surface of the probe clamping sleeve 11 matches the end portion of the ultrasonic probe 2, and the shape of the solid-state coupling member 12 matches the end surface of the probe clamping sleeve 11, e.g., when the ultrasonic probe 2 is a convex array probe, the probe clamping sleeve 11 has an arc-shaped end surface and the solid-state coupling member 12 is an arc-shaped solid-state coupling member 12, and when the ultrasonic probe 2 is a linear array probe, the probe clamping sleeve 11 has a planar end surface and the solid-state coupling member 12 is a flat and straight solid-state coupling member 12.

Optionally, the ultrasonic probe coupling assembly 1 further comprises an elastic gasket 14, the elastic gasket 14 is disposed on the probe clamping sleeve 11, and when the ultrasonic probe 2 is inserted into the probe clamping sleeve 11, the elastic gasket 14 is sandwiched between the probe clamping sleeve 11 and the ultrasonic probe 2. The size of the inner hole of the probe clamping sleeve 11 is larger than the size of the ultrasonic probe 2. When the ultrasonic probe 2 is inserted into the probe clamping sleeve 11, the elastic gasket 14 is elastically deformed, while producing an elastic restoring force, which eliminates the gap between the ultrasonic probe 2 and the probe clamping sleeve 11, thereby fixing the ultrasonic probe 2.

The elastic gasket 14 has a certain clamping size margin, and can form an adaptive clamping for the ultrasonic probes 2 that do not differ greatly in size, and for the ultrasonic probes 2 that differ greatly in size, elastic gaskets 14 different in thickness can be used to adapting, so that the ultrasonic probe coupling assembly 1 of the present disclosure can be adapted to ultrasonic probes 2 of a variety of sizes and types Optionally, the opening of the probe clamping sleeve 11 is square, and four elastic gaskets 14 are provided on the four sides of the opening of the probe clamping sleeve 11 to clamp the ultrasonic probe 2 in the circumferential direction, so that good matching is formed between the probe clamping sleeve 11 and the ultrasonic probe 2.

The elastic gasket 14 is detachable from the probe clamping sleeve 11, and by using different elastic gaskets 14, i.e., by enabling the elastic gaskets 14 to protrude from the inner wall of the probe clamping sleeve 11 by different thicknesses, the adaptability of the probe clamping sleeve 11 can be further enhanced.

Optionally, the probe clamping sleeve 11 is provided with an inserting groove 113, the elastic gasket 14 is provided with an inserting block 141, and the elastic gasket 14 is inserted into the inserting groove 113 through the inserting block 141, thereby realizing the fixing of the elastic gasket 14 to the probe clamping sleeve 11. The inserting groove 113 on the probe clamping sleeve 11 is provided with a position-limiting structure so that the elastic gasket 14 is not easily released from the probe clamping sleeve 11 after insertion.

Optionally, the inserting groove 113 on the probe clamping sleeve 11 is provided with a position-limiting groove 114, and the position-limiting groove 114 is a through groove having a width larger than the strip-like inserting groove 113, and may specifically be a circular through groove. The inserting block 141 on the elastic gasket 14 is strip-shaped, and the strip-shaped inserting block 141 is provided with a position-limiting protrusion 142 corresponding to the position-limiting groove 114. When the inserting block 141 is inserted into the inserting groove 113, the position-limiting protrusion 142 is deformed relative to the inserting groove 113, and the insertion is continued, so that the position-limiting protrusion 142 is embedded into the position-limiting groove 114, thereby finishing the mounting of the elastic gasket 14. When the elastic gasket 14 is detached from the probe clamping sleeve 11, the position-limiting protrusion 142 forms a certain obstacle to the pullout of the elastic gasket 14. At the time of pulling out the elastic gasket 14, it is necessary to press the position-limiting protrusion 142 to pull it out, which therefore increases the engagement force between the elastic gasket 14 and the probe clamping sleeve 11.

The elastic gasket 14 is a rubber gasket, and may also be a gasket made of a soft, easily deformable and elastic material, such as a foam gasket.

It will be appreciated that, optionally, rubber gaskets in other numbers and of other types may also be provided on the probe clamping sleeve 11, e.g., the elastic gasket 14 is a one-piece member that matches the opening of the probe clamping sleeve 11 and is sleeved on the opening of the probe clamping sleeve 11; the elastic gasket 14 may also be directly fixed to the inner side of the probe clamping sleeve 11; and in addition to being provided on the straight side of the probe clamping sleeve 11, the elastic gasket 14 may also be provided on the corner of the probe clamping sleeve 11, or on both the straight side and the corner. All the elastic gaskets 14 that can be fixed on the probe clamping sleeve 11 and can be clamped between the probe clamping sleeve 11 and the ultrasonic probe 2 to eliminate the gap between the ultrasonic probe 2 and the probe clamping sleeve 11 will fall within the protection scope claimed in the present disclosure.

Optionally, the radius of curvature of the side of the solid-state coupling member 12 in contact with the ultrasonic probe 2 is not smaller than the radius of curvature of the ultrasonic probe 2, so that the solid-state coupling member 12 can be brought into close contact with the end portion of the ultrasonic probe 2, so as to eliminate the gap between the solid-state coupling member 12 and the ultrasonic probe 2 as much as possible.

The radius of curvature of the side of the solid-state coupling member 12 in contact with the skin is not greater than the radius of curvature of the ultrasonic probe 2. Due to the characteristic of unevenness of the human body surface, by making the end of the solid-state coupling member 12 in contact with the skin have a certain radian, it is possible to make the solid-state coupling member 12 match the uneven human body contact surface, so as to eliminate the air between the solid-state coupling member 12 and the skin as much as possible, and optimize the transmission effect of the ultrasonic waves in the ultrasonic probe coupling assembly 1.

As described above, the ultrasonic probe coupling assembly 1 and the ultrasonic probe 2 constitute an ultrasonic probe mechanism.

Figures 8, 9:
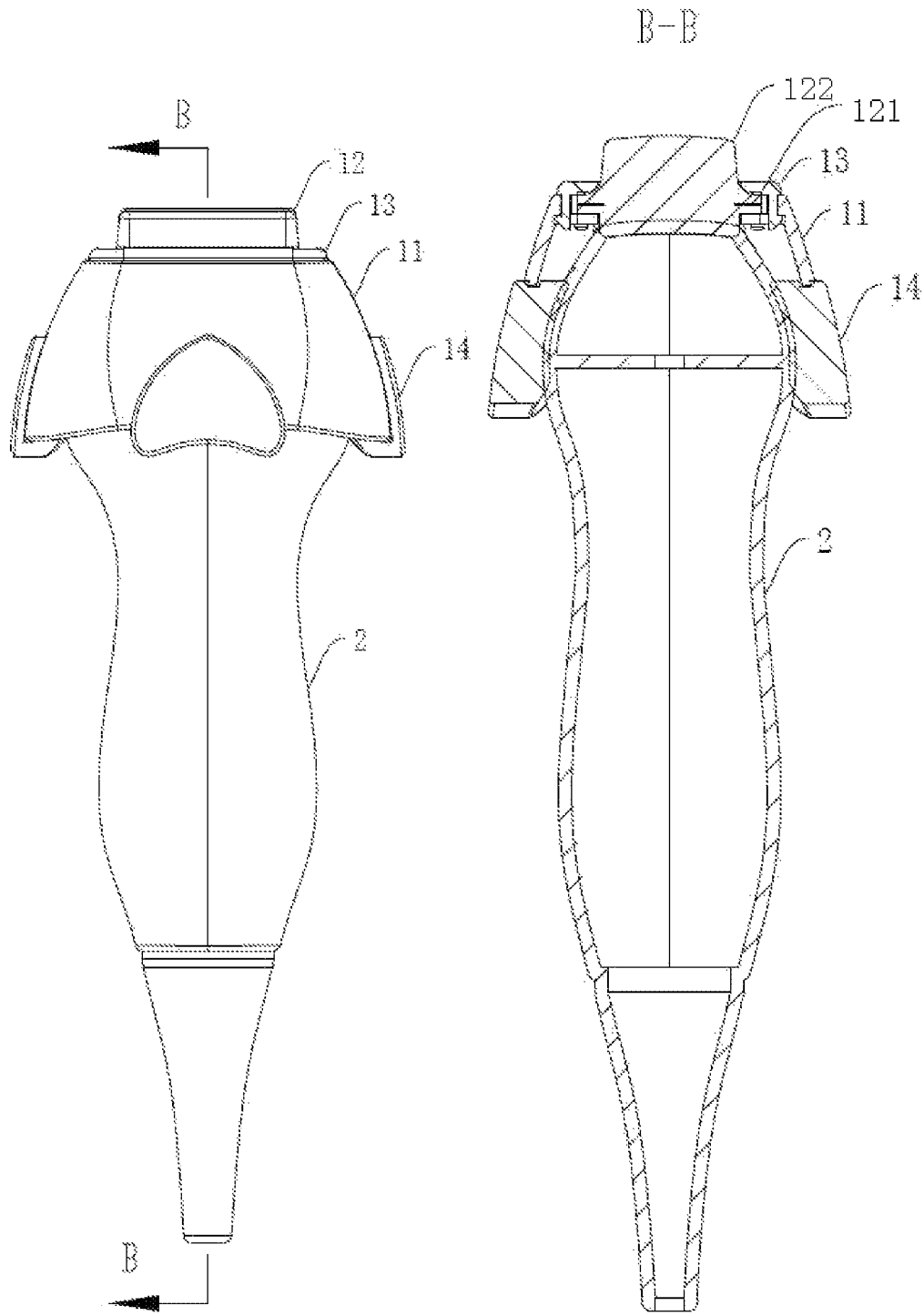
FIG. 8 is a front view of overall structure of the ultrasonic probe coupling assembly provided by the present disclosure.
FIG. 9 is a B-B sectional structure schematic view of FIG. 8.
Figure 10:
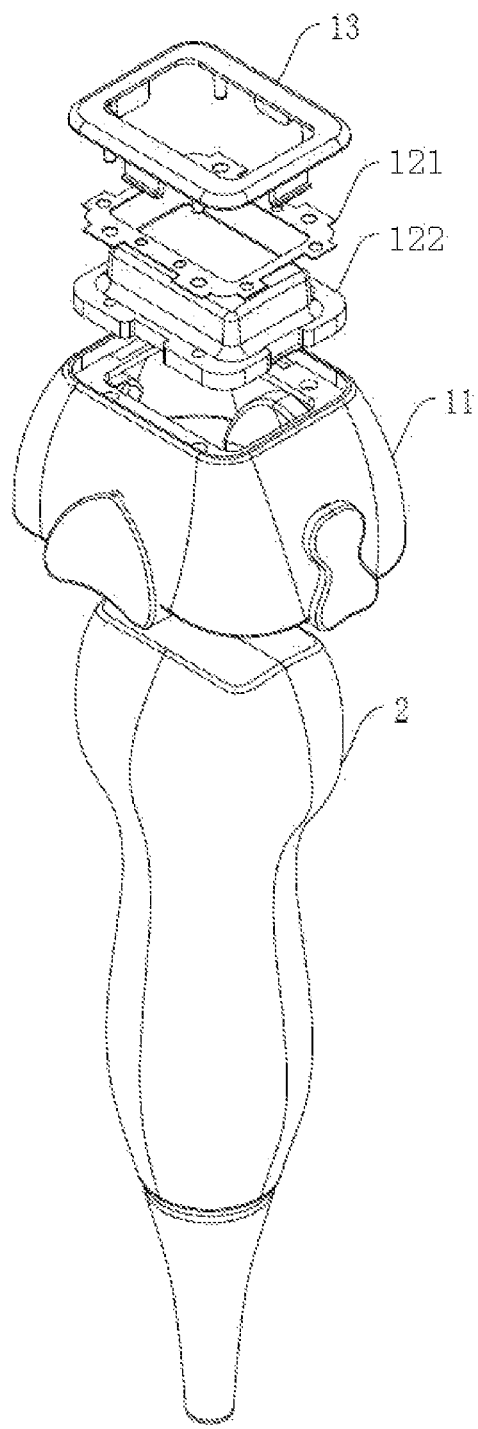
FIG. 10 is an exploded structure schematic view of the ultrasonic probe coupling assembly provided by the present disclosure.

Referring to FIGS. 8-10 together, optionally, the solid-state coupling member 12 comprises a plastic portion 121 and a solid-state coupling portion 122. The plastic portion 121 is embedded into the solid-state coupling portion 122, so that the solid-state coupling member 12 is integrally formed. The plastic portion 121 is formed as an annular protrusion of the solid-state coupling member 12, and the solid-state coupling member 12 is fixed in the probe clamping sleeve 11 by the plastic portion 121. By embedding the plastic portion 121 in the solid-state coupling portion 122, the strength of the connection structure of the solid-state coupling member 12 is enhanced and the solid-state coupling member 12 can be firmly fixed to the probe clamping sleeve 11.

The plastic portion 121 is directly molded in the solid-state coupling portion 122. As shown in FIG. 10, in order to clearly reflect the structure of the plastic portion 121, the plastic portion 121 is separated from the solid-state coupling portion 122. The solid-state coupling portion 122 is provided with an annular protrusion, and the plastic portion 121 is embedded in the annular protrusion of the solid-state coupling portion 122 and has the shape of square frame. The cross section of the solid-state coupling portion 122 matches the size of the inner frame of the connecting frame 115 on the probe clamping sleeve 11, so that the solid-state coupling portion 122 can extend out from the connecting frame 115 to come into close contact with the end portion of the ultrasonic probe 2.

The plastic portion 121 may also be flush with the end surface of the solid-state coupling portion 122, so that the solid-state coupling member 12 becomes a member formed by two stacked cuboids. In other words, the solid-state coupling member 12 is formed by stacking the plastic portion 121 and the solid-state coupling portion 122 on top of each other. The solid-state coupling member 12 abuts against the connecting frame 115, and the ultrasonic probe 2 needs to pass through the connecting frame 115 and then abuts against the solid-state coupling member 12, that is, the solid-state coupling member 12 is in abutment with the connecting frame 115, therefore the ultrasonic probe 2 needs to pass through the section where the connecting frame 115 is located and then comes into abutment with the solid-state coupling member 12.

The ultrasonic probe coupling assembly 1 further comprises a pressing member 13, the pressing member 13 is fixed to the end portion of the probe clamping sleeve 11 for pressing the plastic portion 121, and the solid-state coupling portion 122 protrudes from the pressing member 13. The pressing member 13 is pressed against the plastic portion 121, so that the plastic portion 121 is sandwiched between the pressing member 13 and the connecting frame 115 in the probe clamping sleeve 11, and in this way, the solid-state coupling member 12 is fixed to the probe clamping sleeve 11. The pressing member 13 is provided with a fixing claw 132, and the probe clamping sleeve 11 is correspondingly provided with a through groove/recess to be engaged with the fixing claw 132. Moreover, the fixing portion 123 is provided with a relief groove 120 corresponding to the fixing claw 132, allowing the fixing claw 132 to pass through and to be clamped in the through groove/recess.

Optionally, the pressing member 13 may be omitted, and a connecting structure, i.e., the fixing claw 132, is provided directly on the plastic portion 121. The plastic portion 121 is made of rigid plastic, and the solid-state coupling member 12 is fixed to the probe clamping sleeve 11 through the plastic portion 121, and is in clamping connection with the elastic clamping sleeve.

Optionally, the ultrasonic probe is a phased array probe and a linear array probe, the radius of curvature of the side of the solid-state coupling member 12 in contact with the ultrasonic probe 2 is not smaller than the radius of curvature of the ultrasonic probe 2, so that the solid-state coupling member 12 can be brought into close contact with the end portion of the ultrasonic probe 2, so as to eliminate the gap between the solid-state coupling member 12 and the ultrasonic probe 2 as much as possible.

The radius of curvature of the side of the solid-state coupling member 12 in contact with the skin is not greater than the radius of curvature of the ultrasonic probe 2. Due to the characteristic of unevenness of the human body surface, by making the end of the solid-state coupling member 12 in contact with the skin have a certain radian, it is possible to make the solid-state coupling member 12 match the uneven human body contact surface, so as to eliminate the air between the solid-state coupling member 12 and the skin as much as possible, and optimize the transmission effect of the ultrasonic waves in the ultrasonic probe coupling assembly 1.

As described above, the ultrasonic probe coupling assembly 1 and the ultrasonic probe 2 constitute an ultrasonic probe mechanism.

Optionally, the solid-state coupling member 12 is provided separately from the probe clamping sleeve 11, after injection molding of the solid-state coupling member 12 through a coupling gel, the protruding portion 124 and the fixing portion 123 connected to each other are formed, and the pressing member 13 fixes the solid-state coupling member 12 to the probe clamping sleeve 11 by pressing the fixing portion 123 against the probe clamping sleeve 11.

As described above, the ultrasonic probe coupling assembly 1 and the ultrasonic probe 2 constitute an ultrasonic probe mechanism.

The following contents are further disclosed in the present disclosure:

Referring to FIGS. 1 and 2 together, the present disclosure provides an ultrasonic probe mechanism, comprising an ultrasonic probe coupling assembly 1 and an ultrasonic probe 2. By connecting the ultrasonic probe coupling assembly 1 to the ultrasonic probe 2, the use of an ultrasonic coupling agent can be omitted. The ultrasonic probe coupling assembly 1 comprises a probe clamping sleeve 11 and a solid-state coupling member 12. The solid-state coupling member 12 is fixed to the probe clamping sleeve 11, and the probe clamping sleeve 11 is sleeved on the ultrasonic probe 2, thereby fixing the solid-state coupling member 12 to the ultrasonic probe 2.

One side of the solid-state coupling member 12 is located in the probe clamping sleeve 11 for attachment to the ultrasonic probe 2, and the other side of the solid-state coupling member 12 protrudes from the probe clamping sleeve 11 for contact with the skin. At the time of mounting the ultrasonic probe coupling assembly 1 on the ultrasonic probe 2, the ultrasonic probe 2 is inserted into the probe clamping sleeve 11, and by pushing the ultrasonic probe 2, the end portion of the ultrasonic probe 2 is attached to the solid-state coupling member 12 located at the inner side of the probe clamping sleeve 11, so that seamless transition or nearly seamless transition is realized between the ultrasonic probe 2 and the skin, air between the ultrasonic probe 2 and the skin is eliminated, and stable and effective transmission of the ultrasonic waves is ensured.

Referring to FIGS. 3-6 together, the ultrasonic probe coupling assembly 1 further comprises an elastic gasket 14, the elastic gasket 14 is disposed on the probe clamping sleeve 11, and when the ultrasonic probe 2 is inserted into the probe clamping sleeve 11, the elastic gasket 14 is sandwiched between the probe clamping sleeve 11 and the ultrasonic probe 2. The size of the inner hole of the probe clamping sleeve 11 is larger than the size of the ultrasonic probe 2. When the ultrasonic probe 2 is inserted into the probe clamping sleeve 11, the elastic gasket 14 is elastically deformed, while producing an elastic restoring force, which eliminates the gap between the ultrasonic probe 2 and the probe clamping sleeve 11, thereby fixing the ultrasonic probe 2.

The elastic gasket 14 has a certain clamping size margin, and can form an adaptive clamping for the ultrasonic probes 2 that do not differ greatly in size, and for the ultrasonic probes 2 that differ greatly in size, elastic gaskets 14 different in thickness can be used to adapting, so that the ultrasonic probe coupling assembly 1 of the present disclosure can be adapted to ultrasonic probes 2 of a variety of sizes and types.

Optionally, the opening of the probe clamping sleeve 11 is square, and four elastic gaskets 14 are provided on the four sides of the opening of the probe clamping sleeve 11 to clamp the ultrasonic probe 2 in the circumferential direction, so that good matching is formed between the probe clamping sleeve 11 and the ultrasonic probe 2.

The elastic gasket 14 is detachable from the probe clamping sleeve 11, and by using different elastic gaskets 14, i.e., by enabling the elastic gaskets 14 to protrude from the inner wall of the probe clamping sleeve 11 by different thicknesses, the adaptability of the probe clamping sleeve 11 can be further enhanced.

The elastic gasket 14 is connected to the probe clamping sleeve 11 by means of plugging-in connection, which is a detachable connection that is convenient to assemble and disassemble, is simple in structure and does not need the help of other connecting parts.

Optionally, the probe clamping sleeve 11 is provided with an inserting groove 113, and the elastic gasket 14 is correspondingly provided with an inserting block 141. By inserting the inserting block 141 into the inserting groove 113, the elastic gasket 14 is inserted into the probe clamping sleeve 11. The opening surface of the probe clamping sleeve 11, that is, the side wall of the opened probe clamping sleeve 11 on the side into which the ultrasonic probe 2 is inserted, is provided with an inserting groove 113, and the inserting groove 113 extends downwards from the end surface of the probe clamping sleeve 11. The elastic gasket 14 is in the form of a sheet, with a ⊏-shaped groove formed in the middle. The elastic gasket 14 is in a ⊏-shape as viewed from the side, and the width of the ⊏-shaped opening matches the thickness of the probe clamping sleeve 11. The ⊏-shaped elastic gasket 14 includes a public side and two parallel sides, and the inserting block 141 is provided between the two parallel sides to connect the two parallel sides. When the elastic gasket 14 is connected to the probe clamping sleeve 11, the inserting block 141 is inserted into the inserting groove 113, the inner side of the public side abuts against the end surface of the probe clamping sleeve 11, one of the two parallel sides attaches to the inner wall of the probe clamping sleeve 11, the other one of the two parallel sides attaches to the outer wall of the probe clamping sleeve 11, and the elastic gasket 14 located at the inner side of the probe clamping sleeve 11 serves to clamp the ultrasonic probe 2.

The inserting groove 113 is provided with a position-limiting groove 114, and the inserting block 141 is inserted into the position-limiting groove 114 so as to limit the elastic gasket 14 from being separated from the probe clamping sleeve 11. After the elastic gasket 14 is inserted into the probe clamping sleeve 11, the elastic gasket 14 still has the freedom to move in a direction opposite to the insertion direction, and by providing the corresponding position-limiting groove 114, the inserting block 141 can be fixed after being inserted into the inserting groove 113, and the freedom of the elastic gasket 14 can be completely limited.

Specifically, the position-limiting groove 114 may be a groove perpendicular to the inserting groove 113, the position-limiting groove 114 and the inserting groove 113 constitute an L-shaped groove, the inserting block 141 on the elastic gasket 14 has a width matching the width of the inserting groove 113 and a length matching the width of the position-limiting groove 114, and the distance between the inserting block 141 and the public side of the elastic gasket 14 is not smaller than the length of the inserting groove 113. At the time of assembling the elastic gasket 14, the inserting block 141 is inserted into the inserting groove 113 and pushed inwards, and when pushed to the position of the position-limiting groove 114, the inserting block 141 is pushed transversely to limit the freedom of the inserting block 141 to move in a direction parallel to the inserting groove 113, thereby limiting the release of the elastic gasket 14 from the probe clamping sleeve 11.

Optionally, the inserting block 141 is correspondingly provided with a position-limiting protrusion 142 protruding from the inserting block 141, and the position-limiting protrusion 142 is embedded into the position-limiting groove 114 when the inserting block 141 is inserted into the inserting groove 113. The inserting block 141 is a strip-shaped body simultaneously connected between the public side and the two parallel sides of the elastic gasket 14, the inserting groove 113 is in the shape of a strip-shaped groove that cooperates with the inserting block 141, and the inserting groove 113 is correspondingly provided with a position-limiting groove 114. When the inserting block 141 is inserted into the inserting groove 113, the position-limiting protrusion 142 is deformed relative to the inserting groove 113, and the insertion is continued, so that the position-limiting protrusion 142 is embedded into the position-limiting groove 114, thereby finishing the mounting of the elastic gasket 14. When the elastic gasket 14 is detached from the probe clamping sleeve 11, the position-limiting protrusion 142 forms a certain obstacle to the pullout of the elastic gasket 14. At the time of pulling out the elastic gasket 14, it is necessary to press the position-limiting protrusion 142 to pull it out, which therefore increases the engagement force between the elastic gasket 14 and the probe clamping sleeve 11.

Optionally, the position-limiting protrusion 142 is in a cylindrical shape, and the position-limiting groove 114 is a circular groove. A cylinder is a poleless structure and has a good guiding property, which facilitates the assembly of the elastic gasket 14.

Optionally, the inserting groove 113 may be a blind groove provided on the probe clamping sleeve 11, and the elastic gasket 14 is provided at the inner side of the probe clamping sleeve 11. Rubber gaskets in other numbers and of other types may also be provided on the probe clamping sleeve 11, e.g., the elastic gasket 14 is a one-piece elastic sleeve adapted to the opening of the probe clamping sleeve 11 and is sleeved on the opening of the probe clamping sleeve 11, attaching to both the inner wall and the outer wall of the probe clamping sleeve 11 at the same time; and in addition to being provided on the straight side of the probe clamping sleeve 11, the elastic gasket 14 may also be provided on the corner of the probe clamping sleeve 11, or on both the straight side and the corner. All the elastic gaskets 14 that can be fixed on the probe clamping sleeve 11 and can be clamped between the probe clamping sleeve 11 and the ultrasonic probe 2 to eliminate the gap between the ultrasonic probe 2 and the probe clamping sleeve 11 will fall within the protection scope claimed in the present disclosure.

The elastic gasket 14 at the inner side of the probe clamping sleeve 11 has an outwardly flared guiding slope at the end close to an opening surface of the probe clamping sleeve 11, and the elastic gasket 14 extending towards the inner side of the probe clamping sleeve 11 has a clamping surface that matches the ultrasonic probe 2, so that the probe clamping sleeve 11 has a good guiding property for the insertion of the ultrasonic probe, and meanwhile, the clamping effect of the probe clamping sleeve 11 on the ultrasonic probe 2 is further optimized as a clamping surface matching the ultrasonic probe 2 is provided on the elastic gasket 14. It will be appreciated that the elastic gasket 14 may be detached and replaced with different types of elastic gaskets 14 so as to match different ultrasonic probes 2.

The elastic gasket 14 is a rubber gasket, and may also be a gasket made of a soft, easily deformable and elastic material, such as a foam gasket.

As described above, there are also several solutions of the ways in which the solid-state coupling member 12 is fixed to the probe clamping sleeve 11, for example, the solid-state coupling member 12 may be pressed against and fixed to the probe clamping sleeve 11 by the pressing member 13, the pressing member 13 is provided with a fixing claw 132, and by engaging the fixing claw 132 with the probe clamping sleeve 11, the solid-state coupling member 12 is fixed. The solid-state coupling member 12 may also be molded on the probe clamping sleeve 11 by casting and then pressed by the pressing member 13, or a plastic frame may be embedded in the solid-state coupling member 12, and the pressing member 13 presses the plastic frame against the probe clamping sleeve 11 so as to fix the solid-state coupling member 12.

As described above, the ultrasonic probe coupling assembly 1 can be applied to various types of ultrasonic probes 2, such as linear array probes, convex array probes, etc.

Figure 11:
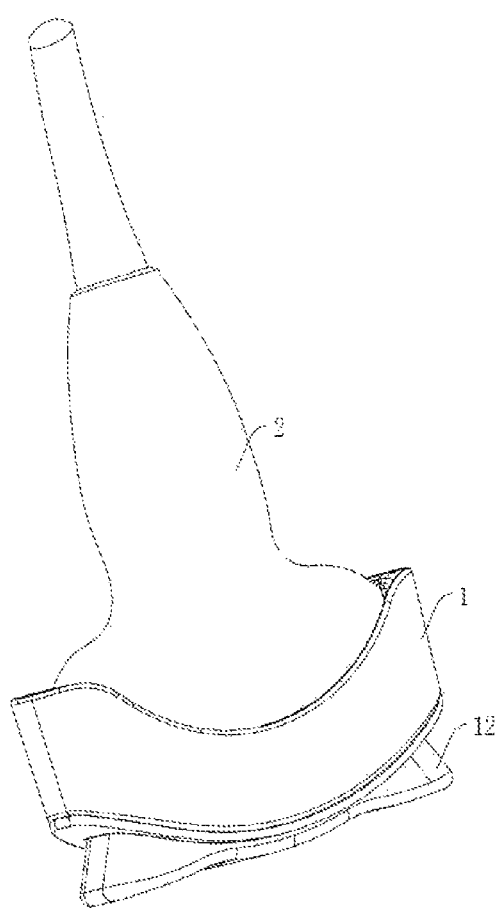
FIG. 11 is an overall structure schematic view of an ultrasonic probe assembly provided by the present disclosure.
Figure 12:
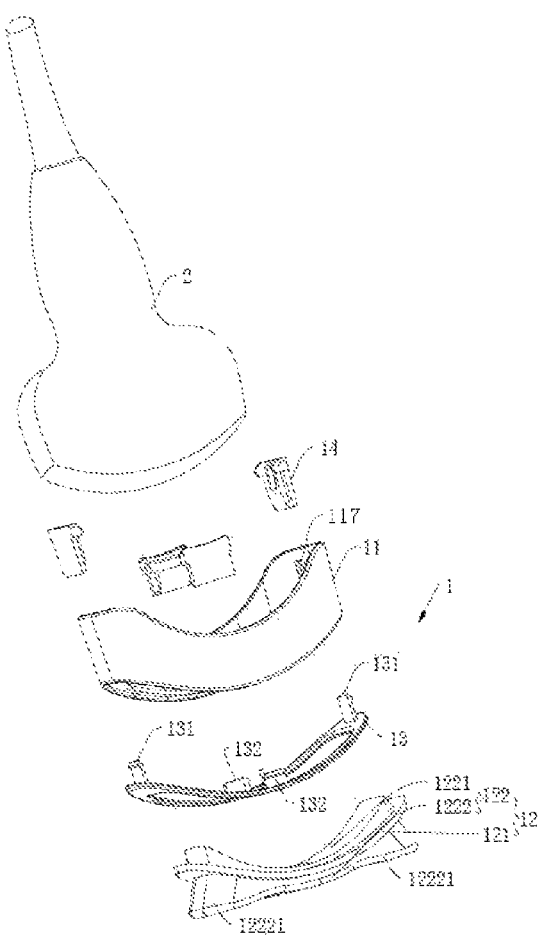
FIG. 12 is an exploded structure schematic view of the ultrasonic probe assembly provided by the present disclosure.
Figure 13:
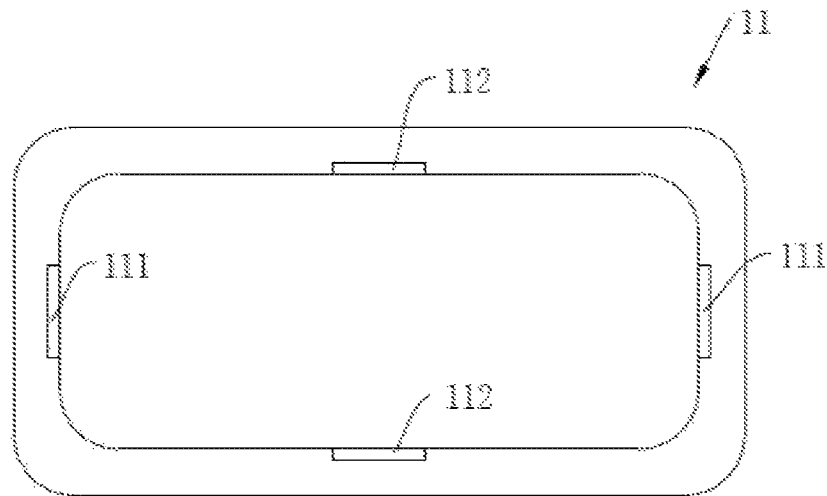
FIG. 13 is a structure schematic view of end surface of the end of a probe clamping sleeve of the ultrasonic probe coupling assembly provided by the present disclosure at which the solid-state coupling member is mounted.

The following contents are further disclosed in the present disclosure:

Referring to FIGS. 11 and 12 together, the ultrasonic probe coupling assembly 1 of the present disclosure can omit the use of an ultrasonic coupling agent by being connected to the ultrasonic probe 2. The ultrasonic probe coupling assembly 1 comprises a probe clamping sleeve 11 and a solid-state coupling member 12. The solid-state coupling member 12 is fixed to the probe clamping sleeve 11, and the probe clamping sleeve 11 is sleeved on the ultrasonic probe 2, thereby fixing the solid-state coupling member 12 to the ultrasonic probe 2.

The solid-state coupling member 12 comprises a plastic portion 121 and a solid-state coupling portion 122. The plastic portion 121 is embedded in the solid-state coupling portion 122 to be integrally connected to the solid-state coupling portion 122, so that the solid-state coupling member 12 is integrally formed. The plastic portion 121 is formed as an annular protrusion on the solid-state coupling member 12, and the solid-state coupling member 12 is fixed to the probe clamping sleeve 11 by the annular protrusion or by providing a connecting structure on the annular protrusion.

One side of the solid-state coupling portion 122 is located in the probe clamping sleeve 11 to be attached to the ultrasonic probe 2, and the other side of the solid-state coupling portion 122 protrudes from the probe clamping sleeve 11 for contact with the skin, thereby allowing seamless transition between the probe and the skin, and ensuring stable and effective transmission of ultrasonic waves.

The plastic portion 121 is deformable together with the solid-state coupling portion 122, the plastic portion 121 and the solid-state coupling portion are both deformable, and when the plastic portion 121 is deformed, the solid-state coupling portion 122 can be driven to be deformed.

On the inner side of the probe clamping sleeve 11 is provided an adjusting locking groove 111 comprising a plurality of locking positions. By engaging the plastic portion 121 with different locking positions, it is possible to adjust the bending degree of the plastic portion 121, that is, the curvature or the position of the plastic portion 121 within the probe clamping sleeve 11, thereby adjusting the position of the solid-state coupling member 12 on the probe clamping sleeve 11 or the curvature thereof, or simultaneously adjusting the position of the solid-state coupling member 12 on the probe clamping sleeve 11 and the curvature thereof.

Optionally, the ultrasonic probe coupling assembly 1 further comprises a pressing member 13, the pressing member 13 is provided with a claw cooperating with the locking positions of the adjusting locking groove 111. By the pressing member 13 covering the plastic portion 121 of the solid-state coupling member 12, i.e., the annular protrusion of the solid-state coupling member 12, and by the claw engaging with the adjusting locking groove 111, the solid-state coupling member 12 is fixed to the probe clamping sleeve 11.

The pressing member 13 is a deformable member, and by clamping the claw on the pressing member 13 in different locking positions of the adjusting locking groove 111, the curvature of the pressing member 13 or the position of the pressing member 13 on the probe clamping sleeve 11 is changed. Since the pressing member 13 covers the side of the plastic portion 121 which is in contact with the skin, when the pressing member 13 is deformed or moved, the solid-state coupling member 12 can be driven to deform or move.

It is to be understood that, optionally, the claw cooperating with the adjusting locking groove 111 may be directly disposed on the plastic portion 121 of the solid-state coupling member 12 and integrally formed with the plastic portion 121.

The plastic portion 121 is made of a kind of plastic having a plastic deformation capability, and the pressing member 13 is made of a kind of plastic having a plastic deformation capability, and has relatively good plastic deformation capability, e.g., common plastics with relatively good plasticity such as PC (polycarbonate), PVC (polyvinyl chloride), PP (polypropylene) or PE (polyethylene).

The plastic portion 121 may be softer than the pressing member 13. When the pressing member 13 is deformed, the plastic portion 121 can be effectively driven to deform and move, and the solid-state coupling portion 122 is softer than the plastic portion 121, thus, it is possible to effectively drive the solid-state coupling portion 122 to deform, thereby effectively driving the solid-state coupling member 12 to deform and move.

The plastic portion 121 is a sheet-like annular frame, and by embedding a gel having an ultrasonic coupling function therein, the plastic portion 121 and the gel having an ultrasonic coupling function are connected into a one-piece member by melting, wherein the gel having an ultrasonic coupling function may be used with reference to the gel of the existing ultrasonic coupling patch, that is, the solid-state coupling portion 122 may be made of the same material as the ultrasonic coupling patch.

The ultrasonic probe 2 clamping sleeve assembly provided in the present disclosure is applied to a convex array probe, and the solid-state coupling portion 122 is attached to the ultrasonic probe 2 with a cambered attachment surface.

The ultrasonic probe 2 is a flat convex array probe having a difference between length and width, and in a rectangular shape with rounded corners. The length direction is the long shaft direction, and the width direction is the short shaft direction. The cross sections of the probe clamping sleeve 11, the solid-state coupling member 12 and the pressing member 13 match the cross section of the convex array probe, that is, the inner hole of the probe clamping sleeve 11 is flat and matches the ultrasonic probe 2. The annular boss on the solid-state coupling member 12 is in a flat shape, the pressing member 13 is in a frame shape matching the annular boss, and the inside dimension of the pressing member 13 is smaller than the outside dimension of the annular boss.

As shown in FIGS. 12 and 3, the short shaft of the pressing member 13 is provided with a fixing claw 132, the long shaft of the pressing member 13 is provided with an adjusting claw 131, and at the corresponding positions of the probe clamping sleeve 11 are provided a fixing locking groove 112 capable of engaging with the fixing claw 132 and an adjusting locking groove 111 capable of engaging with the adjusting claw 131.

The fixing claw 132 is provided in the middle in the long shaft direction, so that the positions of the middle of the pressing member 13 and the probe clamping sleeve 11 are fixed, that is, the position of the middle of the solid-state coupling member 12 on the probe clamping sleeve 11 is fixed. By engaging the adjusting claws 131 on both sides of the pressing member 13 with different positions of the adjusting locking groove 111, the curved radian of the pressing member 13 can be changed, thereby adjusting the curvature of the solid-state coupling member 12, so as to form good matching with the radian of the convex array probe.

Optionally, the inner side of the probe clamping sleeve 11 is provided with adjusting locking grooves 111 in the circumferential direction, and when the adjusting claws 131 simultaneously move on the adjusting locking grooves 111 in the short shaft direction and the long shaft direction, the position of the solid-state coupling member 12 on the probe clamping sleeve 11 is adjusted, thereby adjusting the gap between the solid-state coupling member 12 and the ultrasonic probe 2; and when the adjusting claws 131 move on the adjusting locking grooves 111 at both ends of the long shaft, the curvature of the solid-state coupling member 12 is adjusted, so that the solid-state coupling member 12 is adapted to the curvature of the ultrasonic probe 2.

Optionally, the fixing locking groove 112 comprises a groove body, and two fixing locking grooves 112 are provided at the inner sides of the two ends of the probe clamping sleeve 11 in the short shaft direction, respectively. The hooks on the two fixing claws 132 face away from each other, and are bent towards the probe clamping sleeve 11. The fixing claw 132 is integrally formed with the pressing member 13, has certain elasticity, and is an elastic claw. When the pressing member 13 is pressed down, the fixing claw 132 is deformed, and then restored so that the hook is locked in the fixing locking groove 112 and fixed.

Figure 14:
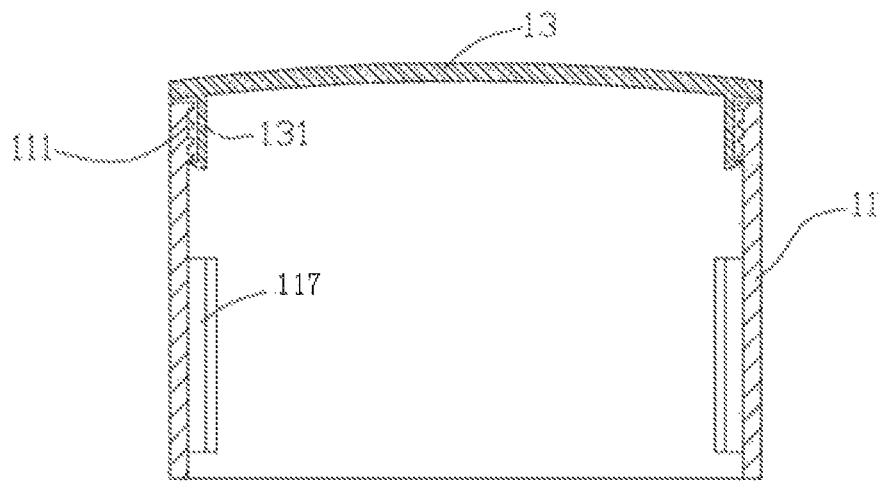
FIG. 14 is a sectional schematic view of the engagement structure between the probe clamping sleeve and a pressing member provided by the present disclosure.

As shown in FIG. 14, the adjusting locking groove 111 comprises a plurality of continuous ratchet teeth, and two adjacent ratchet teeth form a locking position. Each of the inner sides of the two ends of the probe clamping sleeve 11 in the long shaft direction is provided with one adjusting locking groove 111. The hooks of the two adjusting claws 131 face away from each other, and are bent towards the probe clamping sleeve 11. The adjusting claw 131 is integrally formed with the pressing member 13, has certain elasticity, and is an elastic claw. The adjusting claw 131 can be deformed to change its position on the adjusting locking groove 111 to be clamped in different locking positions, thereby changing the degree of bending of the pressing member 13 and adjusting the curvature of the solid-state coupling member 12.

The ratchet teeth are inclined in a direction away from the ultrasonic probe 2, i.e., inclined towards the skin, so that the pressing member 13 moves unidirectionally on the adjusting locking groove 111, the moving direction being from the ultrasonic probe to the skin. The probe clamping sleeve 11 is sleeve-shaped, opened at both ends, with the opening at one end being used for mounting the solid-state coupling member 12 and the opening at the other end being used for inserting the ultrasonic probe 2. Inclined towards the ultrasonic probe 2, i.e., inclined towards the end of the probe clamping sleeve 11 into which the ultrasonic probe 2 is inserted, the two ends of the pressing member 13 can only move towards the skin from the probe, and the radius of curvature of the solid-state coupling member 12 can only be increased. After the ultrasonic probe 2 is inserted into the probe clamping sleeve 11, a pressure is applied to the solid-state coupling member 12, which pressure causes the adjusting claw 131 to move on the adjusting locking groove 111, so that the solid-state coupling member 12 can directly and adaptively attach to the ultrasonic probe 2.

There are several types of radius of curvature of the ultrasonic probe 2 on the market, i.e., R40, R60 and R80. The initial assembly radius of curvature of the solid-state coupling member 12 of the ultrasonic probe 2 clamping sleeve assembly may be set to R40 or less, and when different ultrasonic probes 2 are assembled for use, the solid-state coupling member 12 can be adaptively adjusted, by being applied a force, to a curvature corresponding to the ultrasonic probe 2.

Optionally, the two adjusting claws 131 on the pressing member 13 are inclined, oppositely and inwardly. When the curvature of the pressing member 13 changes, the distance between the two adjusting claws 131 will be changed, specifically, the distance will become larger, which will cause excessive engagement between the adjusting claws 131 and the adjusting locking groove 111. Therefore, by inclining the adjusting claw 131 inwardly, the margin of engagement between the adjusting claw 131 and the adjusting locking groove 111 is increased, when the radius of curvature is relatively large, the deformation of the adjusting claw 131 is relatively large, and when the radius of curvature is reduced, the deformation of the adjusting claw 131 becomes small, preventing excessive engagement of the adjusting claw 131 with the adjusting locking groove 111.

Optionally, the top surface of the adjusting locking groove 111 is inclined outwardly from the solid-state coupling member 12 towards the ultrasonic probe 2, and the top surface of the adjusting locking groove 111 is an outwardly inclined slope. The adjusting locking groove 111 may be provided on the outwardly inclined slope of the solid-state coupling member 12, or the ratchet teeth of the adjusting locking groove 111 may be set to have different tooth heights, so as to compensate for the change in the distance of the adjusting claw 131 when the radius of curvature of the pressing member 13 is reduced, to prevent excessive engagement of the adjusting claw 131 with the adjusting locking groove 111.

Optionally, the solid-state coupling portion 122 comprises a probe engaging portion 1221 and a skin engaging portion 1222 provided on the two sides of the plastic portion 121, the probe engaging portion 1221 is attached to the ultrasonic probe 2, and the skin engaging portion 1222 is attached to the skin. The solid-state coupling portion 122 has a uniform thickness from the plastic portion 121 to the probe engaging portion 1221, the arc of the probe engaging portion 1221 is concentric with the arc of the plastic portion 121, and the probe engaging portion 1221 changes synchronously with the deformation of the plastic portion 121.

The middle portion of the skin engaging portion 1222 is a cambered surface concentric with the cambered surface of the plastic portion 121, with lobes 12221 provided on both sides, and the lobe 12221 is not higher than the middle bulge of the skin engaging portion 1222. Optionally, the middle portion of the skin engaging portion 1222 in the long shaft direction is an arched cambered surface, the cambered surface is concentric with the arc of the plastic portion 121 and changes synchronously with the deformation of the plastic portion 121, with lobes 12221 at both sides, the middle cambered surface and the planes at the two sides are in arc transition, and the skin engaging portion 1222 is planar in the short shaft direction.

The skin engaging portion 1222 is provided with both the cambered surface and the lobes 12221. The cambered surface can ensure that the convex array probe stably transmits the convex array sound waves, and the lobe 12221 can ensure that the air between the convex array ultrasonic probe 2 having a cambered surface at the top and the contact portion of the skin is completely evacuated, thereby enabling a stable fit with the skin, moreover, when the solid-state coupling member 12 is adaptively adjusted with respect to the convex array probe, the lobe 12221 can compensate for the gap formed after the radius of curvature of the solid-state coupling member 12 is reduced.

Optionally, the ultrasonic probe coupling assembly 1 further comprises an elastic gasket 14, the elastic gasket 14 is disposed at the inner side of the probe clamping sleeve 11 and detachable from the probe clamping sleeve 11. The size of the inner hole of the probe clamping sleeve 11 is larger than the size of the ultrasonic probe 2. When the ultrasonic probe 2 is inserted into the probe clamping sleeve 11, the elastic gasket 14 is elastically deformed, while producing an elastic restoring force, which eliminates the gap between the ultrasonic probe 2 and the probe clamping sleeve 11, thereby fixing the ultrasonic probe 2.

The elastic gasket 14 has a certain clamping size margin, and can form an adaptive clamping for the ultrasonic probes 2 that do not differ greatly in size, and for the ultrasonic probes 2 that differ greatly in size, elastic gaskets 14 different in thickness can be used to adapting, so that the ultrasonic probe coupling assembly 1 of the present disclosure can be adapted to ultrasonic probes 2 of a variety of sizes and types Optionally, a plurality of T-shaped grooves are provided at the inner side of the probe clamping sleeve 11 in the circumferential direction, specifically, the four sides of the inner side of the probe clamping sleeve 11 can each be provided with a T-shaped groove, the elastic gasket 14 matches the T-shaped groove, and is fixed by being inserted into the T-shaped groove and forming an interference fit with the T-shaped groove. The interference connection force between the elastic gasket 14 and the T-shaped groove should be set to be greater than the pressing force of the elastic gasket 14 against the ultrasonic probe 2. That is, the amount of interference should be greater than the maximum deformation amount of the elastic gasket 14, in other word, the amount of deformation of the elastic gasket 14 connected to the T-shaped groove is greater than the maximum deformation amount that can be produced by the elastic gasket 14 after being pressed by the ultrasonic probe 2.

The elastic gasket 14 and the probe clamping sleeve 11 form a plug-in connection through the T-shaped groove, and the fixing of the ultrasonic probes 2 of different sizes can be achieved by changing the elastic gaskets 14 of different thicknesses by plugging-in and pulling-out.

The T-shaped groove may be constituted by two L-shaped ribs 117, which are opposed to each other and form a T-shaped groove body with the inner wall of the probe clamping sleeve 11.

Figures 15, 16:
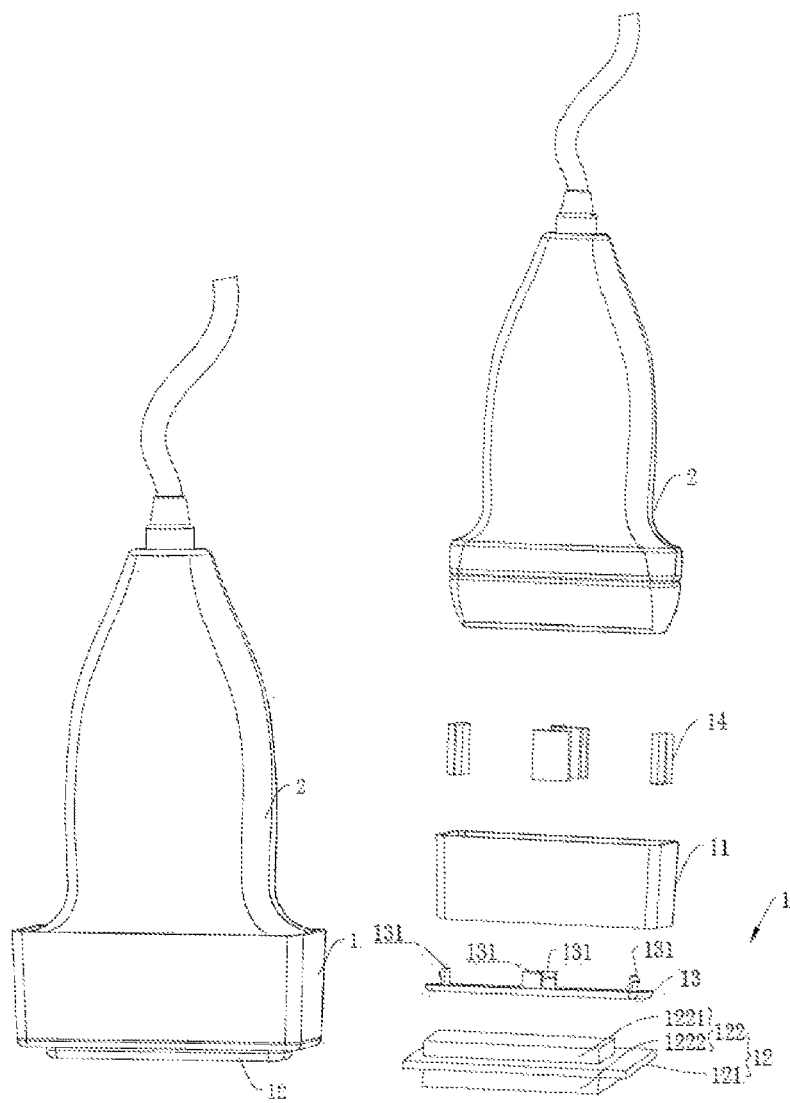
FIG. 15 is an overall structure schematic view of the ultrasonic probe assembly provided by the present disclosure.
FIG. 16 is an exploded structure schematic view of the ultrasonic probe assembly provided by the present disclosure.

Referring to FIGS. 15 and 16 together, optionally, the ultrasonic probe coupling assembly 1 is applied to a linear array ultrasonic probe 2, and the cross sections of the probe clamping sleeve 11, the solid-state coupling member 12 and the pressing member 13 match the cross section of the linear array probe.

The solid-state coupling portion 122 is in a flat plate shape, and the flat frame-shaped plastic portion 121 is fitted on the solid-state coupling portion 122 to form an annular protrusion on the solid-state coupling portion 122. The pressing member 13 is in a flat frame shape.

Figure 17:
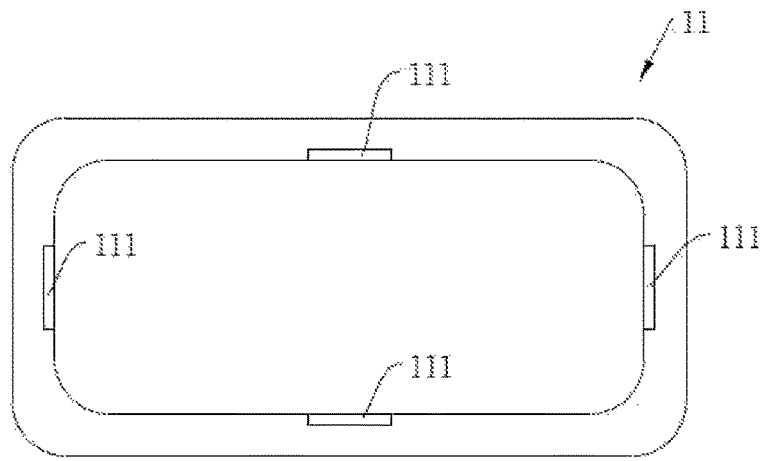
FIG. 17 is a structure schematic view of end surface of the end of a probe clamping sleeve of the ultrasonic probe coupling assembly provided by the present disclosure at which the solid-state coupling member is mounted.

As shown in FIG. 17, an adjusting locking groove 111 is provided at the inner side of the probe clamping sleeve 11 in the circumferential direction, the pressing member 13 is movable on the adjusting locking groove 111 from the skin towards the linear array probe, and when the adjusting claw 131 on the pressing member 13 moves on the adjusting locking groove 111, the distance between the solid-state coupling member 12 and the linear array probe can be adjusted, so that a good fit is formed between the solid-state coupling member 12 and the linear array probe, and the differential gap formed by the assembly of the linear array probe is eliminated.

The present disclosure provides an ultrasonic probe 2 assembly, comprising a convex array probe and the ultrasonic probe 2 clamping sleeve assembly according to the present disclosure.

The present disclosure further provides an ultrasonic probe 2 assembly, comprising a linear array probe and the ultrasonic probe 2 clamping sleeve assembly according to the present disclosure.

In all of the examples illustrated and described herein, any specific value should be interpreted as being illustrative only and not as a limitation. Therefore, other examples of the exemplary embodiments may have different values.

It should be noted that like reference signs and letters denote like items in the following drawings, and therefore, once a certain item is defined in one drawing, it does not need to be further defined or explained in the subsequent drawings.

The above-described embodiments represent only several implementation modes of the present disclosure, the description of which is more specific and detailed, but they should not be construed as limiting the scope of the present disclosure. It should be noted that, for those of ordinary skills in the art, some modifications and improvements may be made without departing from the concept of the present disclosure, and all the modifications and improvements fall within the scope of protection of the present disclosure.

INDUSTRIAL APPLICABILITY

The ultrasonic probe coupling assembly is connected to the ultrasonic probe by means of plugging-in, and has relatively good assemblability. By pushing the ultrasonic probe, the end portion of the ultrasonic probe is attached to the solid-state coupling member located at the inner side of the probe clamping sleeve, so that seamless transition is realized between the ultrasonic probe and the skin, air between the ultrasonic probe and the skin is eliminated, and stable and effective transmission of the ultrasonic waves is ensured.

The ultrasonic probe assembly comprises the ultrasonic probe coupling assembly, there is no need to use a gel coupling agent, and the solid-state coupling member used is capable of forming a good fit with the ultrasonic probe.

By providing an elastic gasket, the elastic gasket has a certain clamping size margin, and can form an adaptive clamping for the ultrasonic probes that do not differ greatly in size, and for the ultrasonic probes that differ greatly in size, elastic gaskets different in thickness can be used to adapting, so that the ultrasonic probe coupling assembly of the present disclosure can be adapted to ultrasonic probes of a variety of sizes and types, thereby forming ultrasonic probe mechanisms having the same ultrasonic probe coupling assembly and different ultrasonic probe sizes.

While fixing the solid-state coupling member to the ultrasonic probe, the ultrasonic probe clamping sleeve assembly can be adapted to convex array probes having different curvatures, and can also eliminate the assembly difference between the ultrasonic probe (including the convex array probe and the linear array probe) and the ultrasonic probe clamping sleeve, and the processing difference of the ultrasonic probe clamping sleeve assembly, enabling a better fit between the solid-state coupling member and the ultrasonic probe.

The ultrasonic probe assembly comprises the ultrasonic probe clamping sleeve assembly, there is no need to use a gel coupling agent, and the solid-state coupling member used is capable of forming a good fit with the ultrasonic probe.

The invention claimed is:

1. An ultrasonic probe coupling assembly, comprising a probe clamping sleeve and a solid-state coupling member,
wherein the probe clamping sleeve is configured to be sleeved on an ultrasonic probe;
the solid-state coupling member is fixed in the probe clamping sleeve, with one side being located in the probe clamping sleeve to be attached to the ultrasonic probe, and an other side protruding from the probe clamping sleeve for contact with a skin;
the ultrasonic probe coupling assembly further comprises an elastic gasket provided on the probe clamping sleeve, wherein when the probe clamping sleeve is sleeved on the ultrasonic probe, the elastic gasket is disposed between the probe clamping sleeve and the ultrasonic probe; and
the probe clamping sleeve is provided with an inserting groove, and the elastic gasket is correspondingly provided with an inserting block.

2. The ultrasonic probe coupling assembly according to claim 1, wherein the solid-state coupling member is fixed in the probe clamping sleeve by injection molding.

3. The ultrasonic probe coupling assembly according to claim 1, wherein the solid-state coupling member comprises a fixing portion and a protruding portion that are integrally molded, the fixing portion is molded to be connected in the probe clamping sleeve and is configured to be attached to the ultrasonic probe, and the protruding portion protrudes from the probe clamping sleeve for contact with the skin.

4. The ultrasonic probe coupling assembly according to claim 1, wherein the solid-state coupling member comprises a plastic portion and a solid-state coupling portion, the plastic portion is embedded in the solid-state coupling portion, so that the solid-state coupling member is integrally formed, the plastic portion is formed as an annular protrusion of the solid-state coupling member, and the solid-state coupling member is fixed in the probe clamping sleeve by the plastic portion.

5. The ultrasonic probe coupling assembly according to claim 1, wherein the ultrasonic probe coupling assembly further comprises a pressing member, the pressing member is fixed at an end portion of the probe clamping sleeve for pressing the solid-state coupling member, and the solid-state coupling member protrudes from the pressing member.

6. The ultrasonic probe coupling assembly according to claim 1, wherein a side of the solid-state coupling member in contact with the ultrasonic probe has a radius of curvature not smaller than a radius of curvature of the ultrasonic probe, and a side of the solid-state coupling member in contact with the skin has a radius of curvature not greater than the radius of curvature of the ultrasonic probe.

7. The ultrasonic probe coupling assembly according to claim 1, wherein the elastic gasket is a rubber gasket or a foam gasket.

8. The ultrasonic probe coupling assembly according to claim 1, wherein the elastic gasket is detachable from the probe clamping sleeve.

9. The ultrasonic probe coupling assembly according to claim 1, wherein the elastic gasket is connected to the probe clamping sleeve by plugging-in.

10. The ultrasonic probe coupling assembly according to claim 1, wherein the inserting groove is provided with a position-limiting groove, and the inserting block is inserted into the position-limiting groove so as to limit the elastic gasket from being separated from the probe clamping sleeve.

11. The ultrasonic probe coupling assembly according to claim 1, wherein the inserting groove is provided with a position-limiting groove, the inserting block is correspondingly provided with a position-limiting protrusion protruding from the inserting block, wherein when the inserting block is inserted into the inserting groove, the position-limiting protrusion is embedded in the position-limiting groove.

12. The ultrasonic probe coupling assembly according to claim 1, wherein the elastic gasket located at an inner side of the probe clamping sleeve has an outwardly flared guiding slope at an end close to an opening surface of the probe clamping sleeve, and the elastic gasket extending towards the inner side of the probe clamping sleeve has a clamping surface that matches the ultrasonic probe.

13. The ultrasonic probe coupling assembly according to claim 1, wherein the elastic gasket is an elastic sleeve that covers an opening of the probe clamping sleeve; or
a plurality of elastic gaskets are provided in a circumferential direction of the opening of the probe clamping sleeve.

14. The ultrasonic probe coupling assembly according to claim 1, wherein the solid-state coupling member comprises a plastic portion and a solid-state coupling portion;
the plastic portion is embedded in the solid-state coupling portion, so that the solid-state coupling member is integrally formed, the plastic portion is formed as an annular protrusion of the solid-state coupling member, and both the plastic portion and the solid-state coupling portion are deformable; and
the inner side of the probe clamping sleeve is provided with an adjusting locking groove comprising a plurality of locking positions, and the plastic portion is capable of adjusting, by engaging with different locking positions, a position of the solid-state coupling member relative to the probe clamping sleeve and/or a curvature of the solid-state coupling member.

15. The ultrasonic probe coupling assembly according to claim 14, wherein the ultrasonic probe coupling assembly further comprises a pressing member, the pressing member is provided with claws cooperating with the locking positions of the adjusting locking groove; and
the pressing member is deformable and covers the plastic portion, and the plastic portion is fixed to the probe clamping sleeve by the pressing member.

16. The ultrasonic probe coupling assembly according to claim 1, wherein the ultrasonic probe is a phased array probe, a linear array probe or a convex array probe, and cross sections of the probe clamping sleeve, the solid-state coupling member and the pressing member match a cross section of the ultrasonic probe.

17. The ultrasonic probe coupling assembly according to claim 15, wherein the ultrasonic probe is a flat convex array probe; and
a short shaft of the pressing member is provided with a fixing claw, and a long shaft of the pressing member is provided with an adjusting claw, and a fixing locking groove capable of engaging with the fixing claw and the adjusting locking groove capable of engaging with the adjusting claw are provided at corresponding positions of the probe clamping sleeve.

18. An ultrasonic probe mechanism, comprising an ultrasonic probe and the ultrasonic probe coupling assembly according to claim 1.

* * * * *